US012703756B2

(12) United States Patent
Shim et al.

(10) Patent No.: US 12,703,756 B2
(45) Date of Patent: Aug. 11, 2026

(54) BCMA-SPECIFIC ANTIBODY AND CHIMERIC ANTIGEN RECEPTOR

(71) Applicants: CUROCELL INC., Daejeon (KR); EWHA UNIVERSITY-INDUSTRY COLLABORATION FOUNDATION, Seoul (KR)

(72) Inventors: Hyunbo Shim, Seoul (KR); Hyung Cheol Kim, Sejong-si (KR); Mi Kyung Kim, Daejeon (KR)

(73) Assignees: CUROCELL INC., Daejeon (KR); EWHA UNIVERSITY-INDUSTRY COLLABORATION FOUNDATION, Seoul (KR)

( * ) Notice: Subject to any disclaimer, the term of this patent is extended or adjusted under 35 U.S.C. 154(b) by 983 days.

(21) Appl. No.: 17/908,823

(22) PCT Filed: Mar. 15, 2021

(86) PCT No.: PCT/KR2021/003135

§ 371 (c)(1),
(2) Date: Jan. 11, 2023

(87) PCT Pub. No.: WO2021/182929

PCT Pub. Date: Sep. 16, 2021

(65) Prior Publication Data

US 2023/0167184 A1 Jun. 1, 2023

(30) Foreign Application Priority Data

Mar. 13, 2020 (KR) ........................ 10-2020-0031211

(51) Int. Cl.

| | |
|---|---|
| ***C07K 16/28*** | (2006.01) |
| ***A61K 40/11*** | (2025.01) |
| ***A61K 40/31*** | (2025.01) |
| ***A61K 40/42*** | (2025.01) |
| ***A61P 35/00*** | (2006.01) |
| ***C12N 5/0783*** | (2010.01) |

(52) U.S. Cl.

CPC .......... *C07K 16/2878* (2013.01); *A61K 40/11* (2025.01); *A61K 40/31* (2025.01); *A61K 40/4215* (2025.01); *A61P 35/00* (2018.01); *C12N 5/0636* (2013.01); *A61K 2239/31* (2023.05); *A61K 2239/38* (2023.05); *A61K 2239/48* (2023.05); *C07K 2317/565* (2013.01); *C07K 2319/02* (2013.01); *C07K 2319/03* (2013.01)

(58) Field of Classification Search

CPC .......... C07K 16/2878; C07K 2317/565; C07K 2319/02; C07K 2319/03; C07K 2317/21; C07K 14/7051; C07K 2317/622; A61K 40/11; A61K 40/31; A61K 40/4215; A61K 2239/31; A61K 2239/38; A61K 2239/48; A61K 35/17; A61P 35/00; C12N 5/0636; C12N 2510/00; C12N 2740/15041

See application file for complete search history.

(56) References Cited

U.S. PATENT DOCUMENTS

| | | | |
|---|---|---|---|
| 2012/0165211 | A1 | 6/2012 | Burioni et al. |
| 2015/0051266 | A1 | 2/2015 | Kochenderfer |
| 2019/0367628 | A1 | 12/2019 | Abujoub et al. |
| 2021/0284749 | A1 | 9/2021 | Park et al. |

FOREIGN PATENT DOCUMENTS

| | | | |
|---|---|---|---|
| JP | 2010-538667 | A | 12/2010 |
| JP | 2017-527271 | A | 9/2017 |
| KR | 10-2013-0129866 | A | 11/2013 |
| KR | 10-2017-0037626 | A | 4/2017 |
| KR | 10-2018-0130534 | A | 12/2018 |
| WO | 2016/014565 | A2 | 1/2016 |
| WO | 2016/094304 | A2 | 6/2016 |
| WO | 2019/089969 | A2 | 5/2019 |
| WO | 2019/195017 | A1 | 10/2019 |
| WO | 2019/196713 | A1 | 10/2019 |
| WO | 2020/004934 | A1 | 1/2020 |

OTHER PUBLICATIONS

Berahovich R, et al. CAR-T Cells Based on Novel BCMA Monoclonal Antibody Block Multiple Myeloma Cell Growth. Cancers (Basel). Sep. 11, 2018;10(9):323. doi: 10.3390/cancers10090323. PMID: 30208593; PMCID: PMC6162381. (Year: 2018).*

* cited by examiner

*Primary Examiner* — Misook Yu
*Assistant Examiner* — Alec Jon Peters
(74) *Attorney, Agent, or Firm* — Bridgeway IP Law Group, PLLC; Jihun Kim

(57) ABSTRACT

An embodiment relates to an anti-BCMA-binding protein and, more specifically, provides an isolated BCMA-binding protein comprising an antigen-binding domain that binds specifically to BCMA, wherein the antigen-binding domain comprises: i) heavy chain variable domain complementarity determining region 1 (VH-CDR1) comprising the amino acid sequence of SEQ ID NO: 1 or an amino acid sequence having at least 80% homology to SEQ ID NO: 1; ii) VH-CDR2 comprising the amino acid sequence of SEQ ID NO: 2 or an amino acid sequence having at least 80% homology to SEQ ID NO: 2; and iii) VH-CDR3 comprising the amino acid sequence of SEQ ID NO: 3 or an amino acid sequence having at least 80% homology to SEQ ID NO: 3.

10 Claims, 12 Drawing Sheets

Specification includes a Sequence Listing.

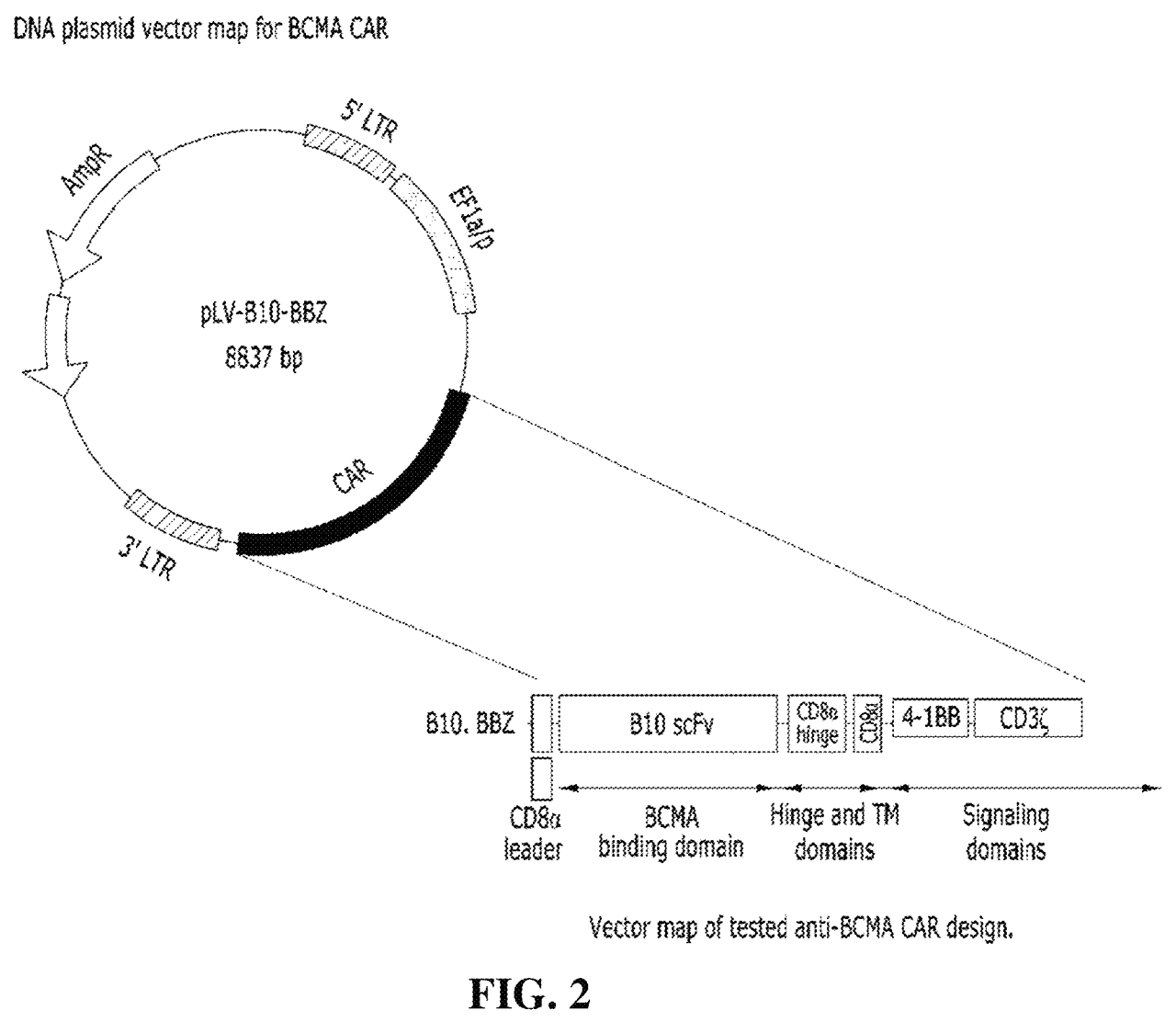

DNA plasmid vector map for BCMA CAR

5' LTR
EF1a/p
AmpR
pLV-B10-BBZ
8837 bp
CAR
3' LTR

B10. BBZ
B10 scFv
CD8α hinge
CD8α
4-1BB
CD3ζ
CD8α leader
BCMA binding domain
Hinge and TM domains
Signaling domains Vector map of tested anti-BCMA CAR design.

FIG. 2

MALPVTALLLPLALLLHAARPEVQLLESGGGLVQPGGSLRLSC
AASGFTFSDYYMSWVRLAPGKGLEWVSAISHSSGNTYYAD
SVKGRFTISRDNSKNTLYLQMNSRAEDTAVYYCAKNNWG
FDYWGQGTLVTVSSGGGGSGGGGSGGGGSQSVLTQPPSA
SGTPGQRVTISCTGSSSNIGSNDVTWYQQLPGTAPKLLIYSD
SKRPSGVPDRFSGSKSGTSASLAISGLRSEDEADYYCAAWD
ASLSGYVFGGGTKLTVLTTTPAPRPPTPAPTIASQPLSLRPEACR
PAAGGAVHTRGLDFACD*IYIWAPLAGTCGVLLLSLVITLY*CKRG
RKKLLYIFKQPFMRPVQTTQEEDGCSCRFPEEEEGGCERVKFSR
SADAPAYKQGQNQLYNELNLGRREEYDVLDKRRGRDPEM
GGKPRRKNPQEGLYNELQKDKMAEAYSEIGMKGERRRGKG
HDGLYQGLSTATKDTYDALHMQALPPR (SEQ ID NO: 15)

| Signal Peptide | α-BCMA scFv | Hinge | *TM* | 4-1BB SD | SD3ζSD |
|---|---|---|---|---|---|

FIG. 3

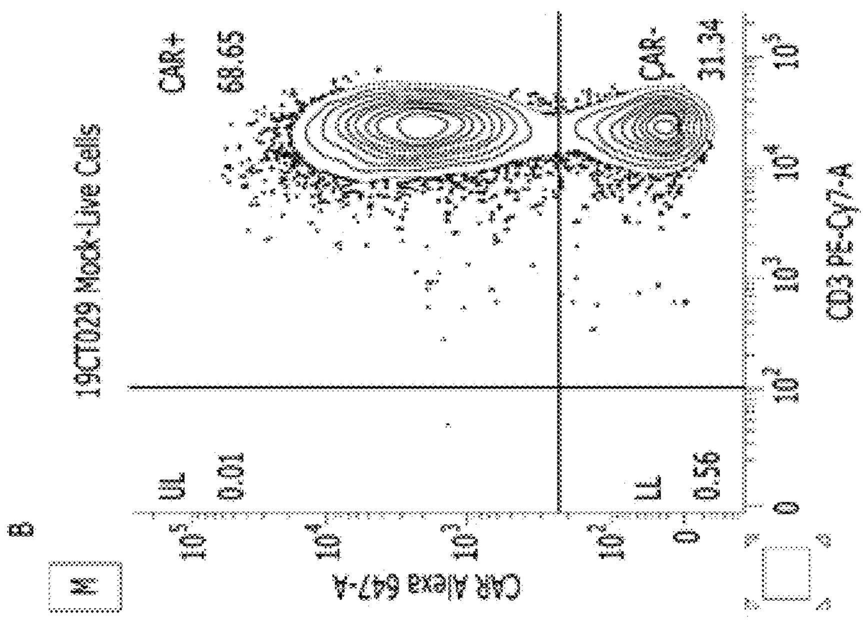
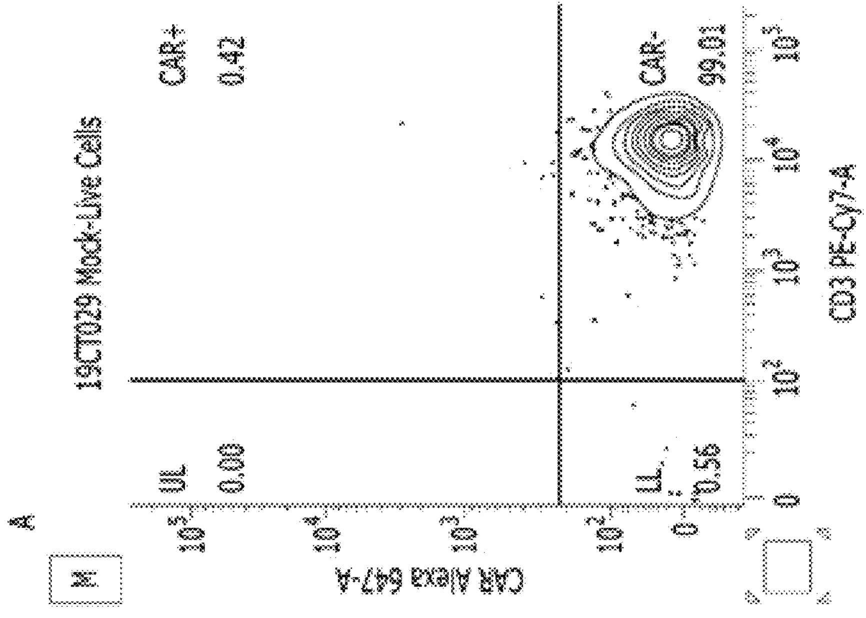
FIG. 4

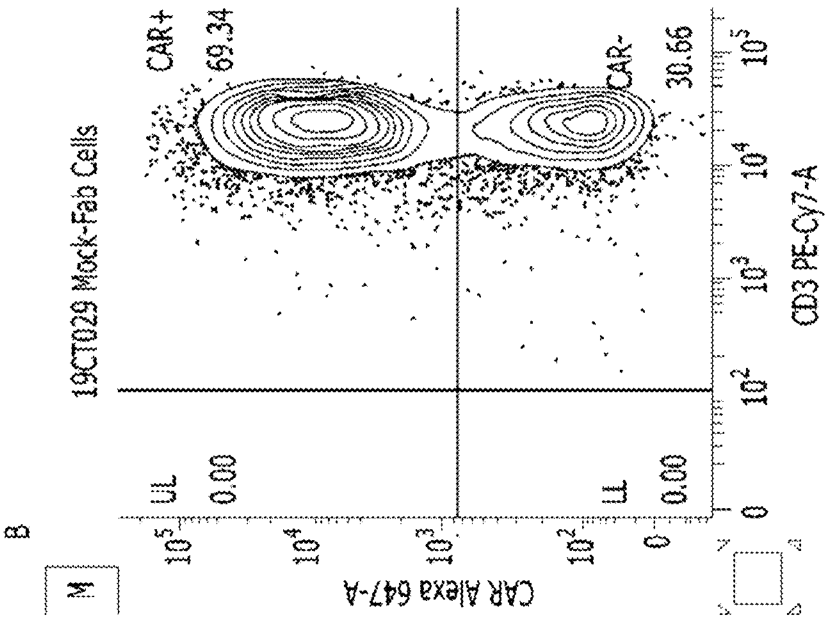
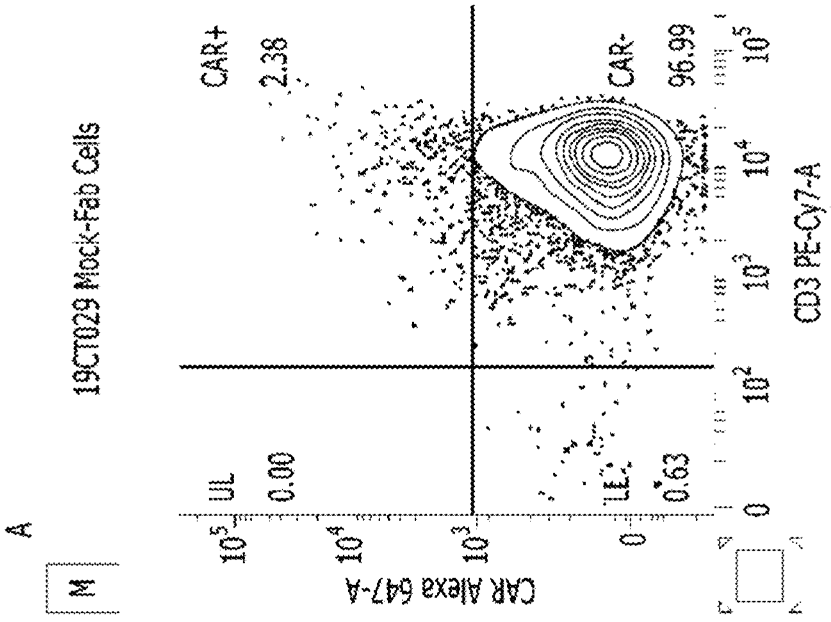
FIG. 5

SEQUENCE LISTING

<160> NUMBER OF SEQ ID NOS: 32

<210> SEQ ID NO 1
<211> LENGTH: 5

```
<212> TYPE: PRT
<213> ORGANISM: Artificial Sequence
<220> FEATURE:
<223> OTHER INFORMATION: VH-CDR1

<400> SEQUENCE: 1

Asp Tyr Tyr Met Ser
1               5


<210> SEQ ID NO 2
<211> LENGTH: 16
<212> TYPE: PRT
<213> ORGANISM: Artificial Sequence
<220> FEATURE:
<223> OTHER INFORMATION: VH-CDR2

<400> SEQUENCE: 2

Ala Ile Ser His Ser Ser Gly Asn Thr Tyr Tyr Ala Asp Ser Val Lys
1               5                   10                  15


<210> SEQ ID NO 3
<211> LENGTH: 9
<212> TYPE: PRT
<213> ORGANISM: Artificial Sequence
<220> FEATURE:
<223> OTHER INFORMATION: VH-CDR3

<400> SEQUENCE: 3

Ala Lys Asn Asn Trp Gly Phe Asp Tyr
1               5


<210> SEQ ID NO 4
<211> LENGTH: 13
<212> TYPE: PRT
<213> ORGANISM: Artificial Sequence
<220> FEATURE:
<223> OTHER INFORMATION: VL-CDR1

<400> SEQUENCE: 4

Thr Gly Ser Ser Ser Asn Ile Gly Ser Asn Asp Val Thr
1               5                   10


<210> SEQ ID NO 5
<211> LENGTH: 7
<212> TYPE: PRT
<213> ORGANISM: Artificial Sequence
<220> FEATURE:
<223> OTHER INFORMATION: VL-CDR2

<400> SEQUENCE: 5

Ser Asp Ser Lys Arg Pro Ser
1               5


<210> SEQ ID NO 6
<211> LENGTH: 11
<212> TYPE: PRT
<213> ORGANISM: Artificial Sequence
<220> FEATURE:
<223> OTHER INFORMATION: VL-CDR3

<400> SEQUENCE: 6

Ala Ala Trp Asp Ala Ser Leu Ser Gly Tyr Val
1               5                   10


<210> SEQ ID NO 7
<211> LENGTH: 116
<212> TYPE: PRT
```

<213> ORGANISM: Artificial Sequence
<220> FEATURE:
<223> OTHER INFORMATION: VH

<400> SEQUENCE: 7

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Asp Tyr
20 25 30

Tyr Met Ser Trp Val Arg Leu Ala Pro Gly Lys Gly Leu Glu Trp Val
35 40 45

Ser Ala Ile Ser His Ser Ser Gly Asn Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Asn Asn Trp Gly Phe Asp Tyr Trp Gly Gln Gly Thr Leu Val
100 105 110

Thr Val Ser Ser
115

<210> SEQ ID NO 8
<211> LENGTH: 110
<212> TYPE: PRT
<213> ORGANISM: Artificial Sequence
<220> FEATURE:
<223> OTHER INFORMATION: VL

<400> SEQUENCE: 8

Gln Ser Val Leu Thr Gln Pro Pro Ser Ala Ser Gly Thr Pro Gly Gln
1 5 10 15

Arg Val Thr Ile Ser Cys Thr Gly Ser Ser Ser Asn Ile Gly Ser Asn
20 25 30

Asp Val Thr Trp Tyr Gln Gln Leu Pro Gly Thr Ala Pro Lys Leu Leu
35 40 45

Ile Tyr Ser Asp Ser Lys Arg Pro Ser Gly Val Pro Asp Arg Phe Ser
50 55 60

Gly Ser Lys Ser Gly Thr Ser Ala Ser Leu Ala Ile Ser Gly Leu Arg
65 70 75 80

Ser Glu Asp Glu Ala Asp Tyr Tyr Cys Ala Ala Trp Asp Ala Ser Leu
85 90 95

Ser Gly Tyr Val Phe Gly Gly Gly Thr Lys Leu Thr Val Leu
100 105 110

<210> SEQ ID NO 9
<211> LENGTH: 241
<212> TYPE: PRT
<213> ORGANISM: Artificial Sequence
<220> FEATURE:
<223> OTHER INFORMATION: scFV

<400> SEQUENCE: 9

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Asp Tyr
20 25 30

Tyr Met Ser Trp Val Arg Leu Ala Pro Gly Lys Gly Leu Glu Trp Val
35 40 45

```
Ser Ala Ile Ser His Ser Ser Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Asn Trp Gly Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Gln Ser Val Leu Thr Gln Pro Pro Ser Ala Ser Gly Thr
    130                 135                 140

Pro Gly Gln Arg Val Thr Ile Ser Cys Thr Gly Ser Ser Ser Asn Ile
145                 150                 155                 160

Gly Ser Asn Asp Val Thr Trp Tyr Gln Gln Leu Pro Gly Thr Ala Pro
                165                 170                 175

Lys Leu Leu Ile Tyr Ser Asp Ser Lys Arg Pro Ser Gly Val Pro Asp
            180                 185                 190

Arg Phe Ser Gly Ser Lys Ser Gly Thr Ser Ala Ser Leu Ala Ile Ser
        195                 200                 205

Gly Leu Arg Ser Glu Asp Glu Ala Asp Tyr Tyr Cys Ala Ala Trp Asp
    210                 215                 220

Ala Ser Leu Ser Gly Tyr Val Phe Gly Gly Gly Thr Lys Leu Thr Val
225                 230                 235                 240

Leu
```

<210> SEQ ID NO 10
<211> LENGTH: 113
<212> TYPE: PRT
<213> ORGANISM: Artificial Sequence
<220> FEATURE:
<223> OTHER INFORMATION: CD3zeta signaling domain

<400> SEQUENCE: 10

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Gly Glu Glu
            20                  25                  30

Tyr Asp Val Leu Asp Lys Arg Arg Gly Arg Asp Pro Glu Met Gly Gly
        35                  40                  45

Lys Pro Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg
```

<210> SEQ ID NO 11
<211> LENGTH: 42
<212> TYPE: PRT
<213> ORGANISM: Artificial Sequence
<220> FEATURE:
<223> OTHER INFORMATION: 41BB signaling domain

<400> SEQUENCE: 11

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40
```

<210> SEQ ID NO 12
<211> LENGTH: 24
<212> TYPE: PRT
<213> ORGANISM: Artificial Sequence
<220> FEATURE:
<223> OTHER INFORMATION: transmembrane domain

<400> SEQUENCE: 12

```
Ile Tyr Ile Trp Ala Pro Leu Ala Gly Thr Cys Gly Val Leu Leu Leu
1               5                   10                  15

Ser Leu Val Ile Thr Leu Tyr Cys
            20
```

<210> SEQ ID NO 13
<211> LENGTH: 45
<212> TYPE: PRT
<213> ORGANISM: Artificial Sequence
<220> FEATURE:
<223> OTHER INFORMATION: hinge domain

<400> SEQUENCE: 13

```
Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45
```

<210> SEQ ID NO 14
<211> LENGTH: 21
<212> TYPE: PRT
<213> ORGANISM: Artificial Sequence
<220> FEATURE:
<223> OTHER INFORMATION: signal peptide

<400> SEQUENCE: 14

```
Met Ala Leu Pro Val Thr Ala Leu Leu Leu Pro Leu Ala Leu Leu Leu
1               5                   10                  15

His Ala Ala Arg Pro
            20
```

<210> SEQ ID NO 15
<211> LENGTH: 480
<212> TYPE: PRT
<213> ORGANISM: Artificial Sequence
<220> FEATURE:
<223> OTHER INFORMATION: a-BCMA CAR

<400> SEQUENCE: 15

```
Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
            20                  25                  30
```

-continued

```
Val Gln Pro Gly Gly Ser Leu Arg Leu Ser Cys Ala Ala Ser Gly Phe
        35                  40                  45

Thr Phe Ser Asp Tyr Tyr Met Ser Trp Val Arg Leu Ala Pro Gly Lys
    50                  55                  60

Gly Leu Glu Trp Val Ser Ala Ile Ser His Ser Ser Gly Asn Thr Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Lys Asn Asn Trp Gly Phe Asp Tyr Trp Gly
        115                 120                 125

Gln Gly Thr Leu Val Thr Val Ser Ser Gly Gly Gly Gly Ser Gly Gly
    130                 135                 140

Gly Gly Ser Gln Ser Val Leu Thr Gln Pro Pro Ser Ala Ser Gly Thr
145                 150                 155                 160

Pro Gly Gln Arg Val Thr Ile Ser Cys Thr Gly Ser Ser Ser Asn Ile
                165                 170                 175

Gly Ser Asn Asp Val Thr Trp Tyr Gln Gln Leu Pro Gly Thr Ala Pro
            180                 185                 190

Lys Leu Leu Ile Tyr Ser Asp Ser Lys Arg Pro Ser Gly Val Pro Asp
        195                 200                 205

Arg Phe Ser Gly Ser Lys Ser Gly Thr Ser Ala Ser Leu Ala Ile Ser
    210                 215                 220

Gly Leu Arg Ser Glu Asp Glu Ala Asp Tyr Tyr Cys Ala Ala Trp Asp
225                 230                 235                 240

Ala Ser Leu Ser Gly Tyr Val Phe Gly Gly Gly Thr Lys Leu Thr Val
                245                 250                 255

Leu Thr Thr Thr Pro Ala Pro Arg Pro Pro Thr Pro Ala Pro Thr Ile
            260                 265                 270

Ala Ser Gln Pro Leu Ser Leu Arg Pro Glu Ala Cys Arg Pro Ala Ala
        275                 280                 285

Gly Gly Ala Val His Thr Arg Gly Leu Asp Phe Ala Cys Asp Ile Tyr
    290                 295                 300

Ile Trp Ala Pro Leu Ala Gly Thr Cys Gly Val Leu Leu Leu Ser Leu
305                 310                 315                 320

Val Ile Thr Leu Tyr Cys Lys Arg Gly Arg Lys Lys Leu Leu Tyr Ile
                325                 330                 335

Phe Lys Gln Pro Phe Met Arg Pro Val Gln Thr Thr Gln Glu Glu Asp
            340                 345                 350

Gly Cys Ser Cys Arg Phe Pro Glu Glu Glu Glu Gly Gly Cys Glu Leu
        355                 360                 365

Arg Val Lys Phe Ser Arg Ser Ala Asp Ala Pro Ala Tyr Gln Gln Gly
    370                 375                 380

Gln Asn Leu Tyr Asn Glu Leu Asn Leu Gly Arg Arg Gly Glu Glu Tyr
385                 390                 395                 400

Asp Val Leu Asp Lys Arg Arg Gly Arg Asp Pro Glu Met Gly Gly Lys
                405                 410                 415

Pro Arg Arg Lys Asn Pro Gln Glu Gly Leu Tyr Asn Glu Leu Gln Lys
            420                 425                 430

Asp Lys Met Ala Glu Ala Tyr Ser Glu Ile Gly Met Lys Gly Glu Arg
        435                 440                 445

Arg Arg Gly Lys Gly His Asp Gly Leu Tyr Gln Gly Leu Ser Thr Ala
```

-continued

```
    450                 455                 460

Thr Lys Asp Thr Tyr Asp Ala Leu His Met Gln Ala Leu Pro Pro Arg
465                 470                 475                 480


<210> SEQ ID NO 16
<211> LENGTH: 18
<212> TYPE: PRT
<213> ORGANISM: Artificial Sequence
<220> FEATURE:
<223> OTHER INFORMATION: Whitlow

<400> SEQUENCE: 16

Gly Ser Thr Ser Gly Ser Gly Lys Pro Gly Ser Gly Glu Gly Ser Thr
1               5                   10                  15

Lys Gly


<210> SEQ ID NO 17
<211> LENGTH: 15
<212> TYPE: PRT
<213> ORGANISM: Artificial Sequence
<220> FEATURE:
<223> OTHER INFORMATION: Lk1

<400> SEQUENCE: 17

Gly Gly Gly Gly Ser Gly Gly Gly Gly Ser Gly Gly Gly Gly Ser
1               5                   10                  15


<210> SEQ ID NO 18
<211> LENGTH: 20
<212> TYPE: PRT
<213> ORGANISM: Artificial Sequence
<220> FEATURE:
<223> OTHER INFORMATION: Lk2

<400> SEQUENCE: 18

Gly Gly Gly Gly Ser Gly Gly Gly Gly Ser Gly Gly Gly Gly Ser Gly
1               5                   10                  15

Gly Gly Gly Ser
            20


<210> SEQ ID NO 19
<211> LENGTH: 5
<212> TYPE: PRT
<213> ORGANISM: Artificial Sequence
<220> FEATURE:
<223> OTHER INFORMATION: Lk3

<400> SEQUENCE: 19

Asp Gly Gly Gly Ser
1               5


<210> SEQ ID NO 20
<211> LENGTH: 5
<212> TYPE: PRT
<213> ORGANISM: Artificial Sequence
<220> FEATURE:
<223> OTHER INFORMATION: Lk4

<400> SEQUENCE: 20

Thr Gly Glu Lys Pro
1               5


<210> SEQ ID NO 21
<211> LENGTH: 4
<212> TYPE: PRT
```

<213> ORGANISM: Artificial Sequence
<220> FEATURE:
<223> OTHER INFORMATION: Lk5

<400> SEQUENCE: 21

Gly Gly Arg Arg
1

<210> SEQ ID NO 22
<211> LENGTH: 14
<212> TYPE: PRT
<213> ORGANISM: Artificial Sequence
<220> FEATURE:
<223> OTHER INFORMATION: Lk6

<400> SEQUENCE: 22

Glu Gly Lys Ser Ser Gly Ser Gly Ser Glu Ser Lys Val Asp
1 5 10

<210> SEQ ID NO 23
<211> LENGTH: 16
<212> TYPE: PRT
<213> ORGANISM: Artificial Sequence
<220> FEATURE:
<223> OTHER INFORMATION: Lk6

<400> SEQUENCE: 23

Lys Glu Ser Gly Ser Val Ser Ser Glu Gln Leu Ala Gln Phe Arg Ser
1 5 10 15

<210> SEQ ID NO 24
<211> LENGTH: 8
<212> TYPE: PRT
<213> ORGANISM: Artificial Sequence
<220> FEATURE:
<223> OTHER INFORMATION: Lk8

<400> SEQUENCE: 24

Gly Gly Arg Arg Gly Gly Gly Ser
1 5

<210> SEQ ID NO 25
<211> LENGTH: 9
<212> TYPE: PRT
<213> ORGANISM: Artificial Sequence
<220> FEATURE:
<223> OTHER INFORMATION: Lk9

<400> SEQUENCE: 25

Leu Arg Gln Arg Asp Gly Glu Arg Pro
1 5

<210> SEQ ID NO 26
<211> LENGTH: 12
<212> TYPE: PRT
<213> ORGANISM: Artificial Sequence
<220> FEATURE:
<223> OTHER INFORMATION: Lk10

<400> SEQUENCE: 26

Leu Arg Gln Lys Asp Gly Gly Gly Ser Glu Arg Pro
1 5 10

<210> SEQ ID NO 27
<211> LENGTH: 16
<212> TYPE: PRT
<213> ORGANISM: Artificial Sequence

```
<220> FEATURE:
<223> OTHER INFORMATION: Lk11

<400> SEQUENCE: 27

Leu Arg Gln Lys Asp Gly Gly Gly Ser Gly Gly Gly Ser Glu Arg Pro
1               5                   10                  15


<210> SEQ ID NO 28
<211> LENGTH: 18
<212> TYPE: PRT
<213> ORGANISM: Artificial Sequence
<220> FEATURE:
<223> OTHER INFORMATION: Lk12

<400> SEQUENCE: 28

Gly Ser Thr Ser Gly Ser Gly Lys Pro Gly Ser Gly Glu Gly Ser Thr
1               5                   10                  15

Lys Gly


<210> SEQ ID NO 29
<211> LENGTH: 726
<212> TYPE: PRT
<213> ORGANISM: Artificial Sequence
<220> FEATURE:
<223> OTHER INFORMATION: pL-B10-BBz

<400> SEQUENCE: 29

Cys Thr Cys Gly Ala Gly Cys Thr Thr Thr Thr Gly Gly Ala Gly Thr
1               5                   10                  15

Ala Cys Gly Thr Cys Gly Thr Cys Thr Thr Thr Ala Gly Gly Thr Thr
            20                  25                  30

Gly Gly Gly Gly Gly Gly Ala Gly Gly Gly Gly Thr Thr Thr Thr Ala
        35                  40                  45

Thr Gly Cys Gly Ala Thr Gly Gly Ala Gly Thr Thr Thr Cys Cys Cys
    50                  55                  60

Cys Ala Cys Ala Cys Thr Gly Ala Gly Thr Gly Gly Gly Thr Gly Gly
65                  70                  75                  80

Ala Gly Ala Cys Thr Gly Ala Ala Gly Thr Thr Ala Gly Gly Cys Cys
                85                  90                  95

Ala Gly Cys Thr Thr Gly Gly Cys Ala Cys Thr Thr Gly Ala Thr Gly
            100                 105                 110

Thr Ala Ala Thr Thr Cys Thr Cys Cys Thr Thr Gly Gly Ala Ala Thr
        115                 120                 125

Thr Thr Gly Cys Cys Cys Thr Thr Thr Thr Thr Gly Ala Gly Thr Thr
    130                 135                 140

Thr Gly Gly Ala Thr Cys Thr Thr Gly Gly Thr Thr Cys Ala Thr Thr
145                 150                 155                 160

Cys Thr Cys Ala Ala Gly Cys Cys Thr Cys Ala Gly Ala Cys Ala Gly
                165                 170                 175

Thr Gly Gly Thr Thr Cys Ala Ala Ala Gly Thr Thr Thr Thr Thr Thr
            180                 185                 190

Thr Cys Thr Thr Cys Cys Ala Thr Thr Thr Cys Ala Gly Gly Thr Gly
        195                 200                 205

Thr Cys Gly Thr Gly Ala Gly Gly Ala Ala Thr Thr Cys Gly Gly Thr
    210                 215                 220

Ala Cys Cys Gly Cys Gly Gly Cys Cys Gly Cys Cys Cys Gly Gly Gly
225                 230                 235                 240

Gly Ala Thr Cys Cys Ala Thr Gly Gly Cys Cys Thr Thr Ala Cys Cys
```

```
                245                 250                 255

Ala Gly Thr Gly Ala Cys Cys Gly Cys Cys Thr Thr Gly Cys Thr Cys
            260                 265                 270

Cys Thr Gly Cys Cys Gly Cys Thr Gly Gly Cys Cys Thr Thr Gly Cys
        275                 280                 285

Thr Gly Cys Thr Cys Cys Ala Cys Gly Cys Cys Gly Cys Cys Ala Gly
    290                 295                 300

Gly Cys Cys Gly Gly Ala Gly Gly Thr Gly Cys Ala Gly Cys Thr Gly
305                 310                 315                 320

Thr Thr Gly Gly Ala Gly Thr Cys Thr Gly Gly Gly Gly Gly Ala Gly
                325                 330                 335

Gly Cys Thr Thr Gly Gly Thr Ala Cys Ala Gly Cys Cys Thr Gly Gly
            340                 345                 350

Gly Gly Gly Gly Thr Cys Cys Cys Thr Gly Ala Gly Ala Cys Thr Cys
        355                 360                 365

Thr Cys Cys Thr Gly Thr Gly Cys Ala Gly Cys Cys Thr Cys Thr Gly
    370                 375                 380

Gly Ala Thr Thr Cys Ala Cys Cys Thr Thr Thr Ala Gly Cys Gly Ala
385                 390                 395                 400

Thr Thr Ala Thr Thr Ala Thr Ala Thr Gly Ala Gly Cys Thr Gly Gly
                405                 410                 415

Gly Thr Cys Cys Gly Cys Cys Thr Gly Gly Cys Thr Cys Cys Ala Gly
            420                 425                 430

Gly Gly Ala Ala Gly Gly Gly Gly Cys Thr Gly Gly Ala Gly Thr Gly
        435                 440                 445

Gly Gly Thr Cys Thr Cys Ala Gly Cys Gly Ala Thr Cys Thr Cys Thr
    450                 455                 460

Cys Ala Thr Ala Gly Thr Ala Gly Thr Gly Gly Thr Ala Ala Thr Ala
465                 470                 475                 480

Cys Ala Thr Ala Thr Thr Ala Cys Gly Cys Thr Gly Ala Thr Thr Cys
                485                 490                 495

Thr Gly Thr Ala Ala Ala Ala Gly Gly Thr Cys Gly Gly Thr Thr Cys
            500                 505                 510

Ala Cys Cys Ala Thr Cys Thr Cys Cys Ala Gly Ala Gly Ala Cys Ala
        515                 520                 525

Ala Thr Thr Cys Cys Ala Ala Gly Ala Ala Cys Ala Cys Gly Cys Thr
    530                 535                 540

Gly Thr Ala Thr Cys Thr Gly Cys Ala Ala Ala Thr Gly Ala Ala Cys
545                 550                 555                 560

Ala Gly Cys Cys Thr Gly Ala Gly Ala Gly Cys Cys Gly Ala Gly Gly
                565                 570                 575

Ala Cys Ala Cys Gly Gly Cys Cys Gly Thr Gly Thr Ala Thr Thr Ala
            580                 585                 590

Cys Thr Gly Thr Gly Cys Gly Ala Ala Ala Ala Ala Thr Ala Ala Thr
        595                 600                 605

Thr Gly Gly Gly Gly Thr Thr Thr Cys Gly Ala Cys Thr Ala Cys Thr
    610                 615                 620

Gly Gly Gly Gly Cys Cys Ala Gly Gly Gly Thr Ala Cys Ala Cys Thr
625                 630                 635                 640

Gly Gly Thr Cys Ala Cys Cys Gly Thr Gly Ala Gly Cys Thr Cys Ala
                645                 650                 655

Gly Gly Thr Gly Gly Ala Gly Gly Cys Gly Gly Thr Thr Cys Ala Gly
            660                 665                 670
```

```
Gly Cys Gly Gly Ala Gly Gly Thr Gly Gly Ala Thr Cys Cys Gly Gly
        675                 680                 685

Cys Gly Gly Thr Gly Gly Cys Gly Gly Ala Thr Cys Gly Cys Ala Gly
    690                 695                 700

Thr Cys Thr Gly Thr Gly Cys Thr Gly Ala Cys Thr Cys Ala Gly Cys
705                 710                 715                 720

Cys Ala Cys Cys Cys Thr
                725
```

<210> SEQ ID NO 30
<211> LENGTH: 477
<212> TYPE: PRT
<213> ORGANISM: Artificial Sequence
<220> FEATURE:
<223> OTHER INFORMATION: pL-B10-BBz

<400> SEQUENCE: 30

```
Cys Thr Gly Thr Gly Cys Thr Gly Ala Cys Thr Cys Ala Gly Cys Cys
1               5                   10                  15

Ala Cys Cys Cys Thr Cys Ala Gly Cys Gly Thr Cys Thr Gly Gly Gly
            20                  25                  30

Ala Cys Cys Cys Cys Cys Gly Gly Gly Cys Ala Gly Ala Gly Gly Gly
        35                  40                  45

Thr Cys Ala Cys Cys Ala Thr Cys Thr Cys Thr Thr Gly Thr Ala Cys
    50                  55                  60

Thr Gly Gly Cys Thr Cys Thr Thr Cys Ala Thr Cys Thr Ala Ala Thr
65                  70                  75                  80

Ala Thr Thr Gly Gly Cys Ala Gly Thr Ala Ala Thr Gly Ala Thr Gly
                85                  90                  95

Thr Cys Ala Cys Cys Thr Gly Gly Thr Ala Cys Cys Ala Gly Cys Ala
            100                 105                 110

Gly Cys Thr Cys Cys Cys Ala Gly Gly Ala Ala Cys Gly Gly Cys Thr
        115                 120                 125

Cys Cys Cys Ala Ala Ala Cys Thr Cys Cys Thr Cys Ala Thr Cys Thr
    130                 135                 140

Ala Thr Thr Cys Thr Gly Ala Thr Ala Gly Thr Ala Ala Gly Cys Gly
145                 150                 155                 160

Gly Cys Cys Ala Ala Gly Cys Gly Gly Gly Thr Cys Cys Cys Thr
                165                 170                 175

Gly Ala Cys Cys Gly Ala Thr Thr Cys Thr Cys Thr Gly Gly Cys Thr
            180                 185                 190

Cys Cys Ala Ala Gly Thr Cys Thr Gly Gly Cys Ala Cys Cys Thr Cys
        195                 200                 205

Ala Gly Cys Cys Thr Cys Cys Cys Thr Gly Gly Cys Cys Ala Thr Cys
    210                 215                 220

Ala Gly Thr Gly Gly Gly Cys Thr Cys Cys Gly Gly Thr Cys Cys Gly
225                 230                 235                 240

Ala Gly Gly Ala Thr Gly Ala Gly Gly Cys Thr Gly Ala Thr Thr Ala
                245                 250                 255

Thr Thr Ala Cys Thr Gly Thr Gly Cys Thr Gly Cys Thr Thr Gly Gly
            260                 265                 270

Gly Ala Thr Gly Cys Thr Ala Gly Cys Cys Thr Gly Ala Gly Thr Gly
        275                 280                 285

Gly Thr Thr Ala Thr Gly Thr Cys Thr Thr Cys Gly Gly Cys Gly Gly
    290                 295                 300
```

-continued

```
Ala Gly Gly Cys Ala Cys Cys Ala Ala Gly Cys Thr Gly Ala Cys Gly
305                 310                 315                 320

Gly Thr Cys Cys Thr Ala Ala Cys Cys Ala Cys Gly Ala Cys Gly Cys
                325                 330                 335

Cys Ala Gly Cys Gly Cys Cys Gly Cys Gly Ala Cys Cys Ala Cys Cys
            340                 345                 350

Ala Ala Cys Ala Cys Cys Gly Gly Cys Gly Cys Cys Cys Ala Cys Cys
        355                 360                 365

Ala Thr Cys Gly Cys Gly Thr Cys Gly Cys Ala Gly Cys Cys Cys Cys
    370                 375                 380

Thr Gly Thr Cys Cys Cys Thr Gly Cys Gly Cys Cys Cys Ala Gly Ala
385                 390                 395                 400

Gly Gly Cys Gly Thr Gly Cys Cys Gly Gly Cys Cys Ala Gly Cys Gly
                405                 410                 415

Gly Cys Gly Gly Gly Gly Gly Gly Cys Gly Cys Ala Gly Thr Gly Cys
            420                 425                 430

Ala Cys Ala Cys Gly Ala Gly Gly Gly Gly Gly Cys Thr Gly Gly Ala
        435                 440                 445

Cys Thr Thr Cys Gly Cys Cys Thr Gly Thr Gly Ala Thr Ala Thr Cys
    450                 455                 460

Thr Ala Cys Ala Thr Cys Thr Gly Gly Gly Cys Gly Cys
465                 470                 475


<210> SEQ ID NO 31
<211> LENGTH: 28
<212> TYPE: PRT
<213> ORGANISM: Artificial Sequence
<220> FEATURE:
<223> OTHER INFORMATION: pL-B10-BBz

<400> SEQUENCE: 31

Gly Ala Thr Thr Ala Gly Thr Thr Cys Thr Cys Gly Ala Gly Cys Thr
1               5                   10                  15

Thr Thr Thr Gly Gly Ala Gly Thr Ala Cys Gly Thr
            20                  25


<210> SEQ ID NO 32
<211> LENGTH: 31
<212> TYPE: PRT
<213> ORGANISM: Artificial Sequence
<220> FEATURE:
<223> OTHER INFORMATION: pL-B10-BBz

<400> SEQUENCE: 32

Gly Gly Gly Cys Gly Cys Cys Cys Ala Gly Ala Thr Gly Thr Ala Gly
1               5                   10                  15

Ala Thr Ala Thr Cys Ala Cys Ala Gly Gly Cys Gly Ala Ala Gly
            20                  25                  30
```

BCMA-SPECIFIC ANTIBODY AND CHIMERIC ANTIGEN RECEPTOR

This application contains a sequence listing in Computer Readable Form (CRF). The CFR file contains the sequence listing entitled "PJK4965686-SequenceListing.txt", which was created on Sep. 1, 2022, and is 13,407 bytes in size. The information in the sequence listing is incorporated herein by reference in entirety.

TECHNICAL FIELD

The present invention relates to a novel protein that binds specifically to BCMA, and more particularly, to a BCMA-binding protein, a nucleic acid encoding the same, a cell comprising the same, and a composition having an anticancer effect, which contains the cell.

BACKGROUND ART

Modified T cell therapy, which has shown excellent effects on cancer treatment, particularly hematological malignancy treatment, is a method of treating cancer using a T-cell genetically engineered to specifically bind to and kill tumor cells in a target molecule-specific manner. Such targeting is generally accomplished by introducing a recombinant DNA molecule encoding a chimeric antigen receptor (CAR) into patient-derived T cells. CARs are synthetic receptors comprising an extracellular targeting domain, a transmembrane domain and one or more intracellular signaling domains. In most cases, the extracellular targeting domain consists of a single-chain Fv fragment (scFv) of an antibody specific to a target molecule, such as a given tumor-associated antigen (TAA). The extracellular targeting domain makes a CAR specific to a tumor, and the intracellular signaling domain activates T cells upon binding of the CAR to the target molecule. These engineered T cells are re-injected into the cancer patients where they specifically bind to and kill cells expressing the CAR-targeted molecule.

A number of clinical studies reporting the effectiveness of CAR T-cell therapy on hematologic malignancies are directed to the treatment of B-cell malignancies, targeting either CD19 or CD20. Although CAR T-cell therapy has emerged as an effective therapy, there is still room for improvement in several aspects, including optimization of CAR signaling, optimization of target antigens, optimization of cell production methods, enhancement of safety, and combination strategies for increasing the therapeutic potential of CAR T-cells.

Multiple myeloma (MM) is a cancer characterized by the accumulation of clonal plasma cells. MM is the second most common blood cancer, and death by MM accounts for 2% of all cancer deaths. MM is a disease whose characteristics are not uniform among patients, and aggressiveness and resistance to treatment thereof significantly differ between patients. For example, while some patients survive 10 years or more after diagnosis, but in some cases, resistance to treatment progresses rapidly and death occurs within 2 years. Although various therapeutic agents have been developed, there is currently no treatment for MM. That is, although existing therapies induce remission of MM, the disease recurs and eventually leads to death in almost all patients, and traditional treatment methods such as chemotherapy and radiotherapy have toxic side effects. Accordingly, there is a need for more effective therapeutic agents for treating MM.

One of the reported potential targets for MM therapy is the B cell maturation antigen (BCMA), a member of the tumor necrosis factor receptor family that is mainly expressed on mature B cells. BCMA is involved in mediating the survival of plasma cells for maintaining long-term humoral immunity in healthy individuals, but recently it has been reported that the expression of BCMA is associated with a number of cancers, autoimmune disorders, and infectious diseases. Cancers with increased expression of BCMA include some hematologic cancers, such as multiple myeloma, Hodgkin's and non-Hodgkin's lymphomas, various leukemias, and glioblastomas. Accordingly, there is a need for effective therapeutic agents that specifically target BCMA-expressing cells.

DISCLOSURE

Technical Problem

The present invention has been made to satisfy the above-mentioned needs, and provides an isolated BCMA-binding protein comprising an antigen-binding domain that binds specifically to BCMA, wherein the antigen-binding domain comprises: i) heavy chain variable domain complementarity determining region 1 (VH-CDR1) comprising the amino acid sequence of SEQ ID NO: 1 or an amino acid sequence having at least 80% homology to SEQ ID NO: 1; ii) VH-CDR2 comprising the amino acid sequence of SEQ ID NO: 2 or an amino acid sequence having at least 80% homology to SEQ ID NO: 2; and iii) VH-CDR3 comprising the amino acid sequence of SEQ ID NO: 3 or an amino acid sequence having at least 80% homology to SEQ ID NO: 3. The present invention also provides an isolated nucleic acid encoding the BCMA-binding protein.

The present invention also provides a cell comprising the nucleic acid encoding the BCMA-binding protein.

The present invention also provides a cell expressing the BCMA-binding protein.

The present invention also provides a composition having an anticancer effect, which contains the cell.

Objects to be achieved by the present invention are not limited to the technical problems mentioned above, and other objects not mentioned herein will be clearly understood to those of ordinary skill in the art to which the present invention pertains from the following description.

Technical Solution

To achieve the above objects, an isolated BCMA-binding protein according to one aspect of the present invention comprises an antigen-binding domain that binds specifically to BCMA, wherein the antigen-binding domain comprises: i) heavy chain variable domain complementarity determining region 1 (VH-CDR1) comprising the amino acid sequence of SEQ ID NO: 1 or an amino acid sequence having at least 80% homology to SEQ ID NO: 1; ii) VH-CDR2 comprising the amino acid sequence of SEQ ID NO: 2 or an amino acid sequence having at least 80% homology to SEQ ID NO: 2; and iii) VH-CDR3 comprising the amino acid sequence of SEQ ID NO: 3 or an amino acid sequence having at least 80% homology to SEQ ID NO: 3.

Here, the antigen-binding domain may further comprise: i) light chain variable domain complementarity determining region 1 (VL-CDR1) comprising the amino acid sequence of SEQ ID NO: 4 or an amino acid sequence having at least 80% homology to SEQ ID NO: 4; ii) VL-CDR2 comprising the amino acid sequence of SEQ ID NO: 5 or an amino acid sequence having at least 80% homology to SEQ ID NO: 5; and iii) VL-CDR3 comprising the amino acid sequence of SEQ ID NO: 6 or an amino acid sequence having at least 80% homology to SEQ ID NO: 6.

The BCMA-binding protein may comprise: a heavy chain variable domain (VH) comprising the amino acid sequence of SEQ ID NO: 7 or an amino acid sequence having at least 80% homology to SEQ ID NO: 7; and a light chain variable domain (VL) comprising the amino acid sequence of SEQ ID NO: 8 or an amino acid sequence having at least 80% homology to SEQ ID NO: 8. The BCMA-binding protein may further comprise a linker, and the linker, VH and VL may be arranged in any one order selected from among VH-linker-VL or VL-linker-VH, in the N-terminal to C-terminal direction.

The BCMA-binding protein may comprise the amino acid sequence of SEQ ID NO: 9 or an amino acid sequence having at least 80% homology to SEQ ID NO: 9.

The BCMA-binding protein may be any one selected from the group consisting of: i) an immunoglobulin selected from among IgA, IgD, IgE, IgG and IgM; ii) a native antibody fragment selected from among Fv, Fab, Fab', F(ab')2, VHH, and VNAR; iii) an engineered antibody selected from among scFv, dsFv, ds-scFv, (scFv)2, diabodies, triabodies, tetrabodies, and pentabodies; iv) ii) or iii) linked to Fc, at least one heavy chain constant domain, multimerization domain or chemical linker, or a combination thereof; and v) an anti-BCMA chimeric antigen receptor (CAR). The anti-BCMA chimeric antigen receptor may further comprise an intracellular signaling domain, wherein the intracellular signaling domain may comprise a signaling domain derived from any one or more selected from among CD3ζ, FcγR, ICOS (CD278), 4-1BB (CD137), OX40 (CD134), CD27, CD28, IL-2RB, IL-15R-α, CD40, MyD88, DAP10, DAP12, MHC class I molecules, TNF receptor proteins, immunoglobulin-like proteins, cytokine receptors, integrins, SLAM protein, activating NK cell receptors, BTLA, Toll ligand receptors, CD2, CD7, CD30, CD40, CDS, ICAM-1, B7-H3, GITR, BAFFR, LIGHT, HVEM (LIGHTR), KIRDS2, SLAMF7, NKp80 (KLRF1), NKp44, NKp30, NKp46, CD19, CD4, CD8α, CD8β, IL2Rγ, IL7Rα, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and CD83-specific ligands. The anti-BCMA chimeric antigen receptor may further comprise a transmembrane domain, wherein the transmembrane domain may be derived from any one selected from among T-cell receptor (TCR) α chains, TCR β chains, CD3ζ, CD3ε, CD28, CD45, CD4, CD5, CD8, CD9, CD16, CD22, CD33, CD37, CD64, CD80, CD86, CD134, CD137, CD154, CD278, and CD314. The anti-BCMA chimeric antigen receptor may further comprise a hinge domain, wherein the hinge domain may be located between the BCMA-binding protein and the transmembrane domain and may be derived from any one selected from CD8, FcγRIIIα, and IgG1. The anti-BCMA chimeric antigen receptor may further comprise a signal peptide at the N-terminus, wherein the signal peptide may be derived from any one selected from CD8, IgG1 heavy chains, IgK light chains, and GM-CSF. The anti-BCMA chimeric antigen receptor may comprise the amino acid sequence of SEQ ID NO: 15 or an amino acid sequence having at least 80% homology to SEQ ID NO: 15.

An isolated nucleic acid according to another aspect of the present invention may encode the above-described BCMA-binding protein.

A cell according to still another aspect of the present invention may comprise the nucleic acid encoding the BCMA-binding protein.

The cell according to still another aspect of the present invention may express the BCMA-binding protein.

A composition having an anticancer effect according to yet another aspect of the present invention comprises either a cell comprising the nucleic acid encoding the BCMA-binding protein, or a cell expressing the BCMA-binding protein.

The above-described technical solution is merely exemplary and should not be construed as limiting the scope of the present invention. In addition to the exemplary embodiments described above, additional embodiments may exist in the accompanying drawings and the detailed description.

Advantageous Effects

The present invention first discloses an isolated BCMA-binding protein comprising an antigen-binding domain that binds specifically to BCMA, wherein the antigen-binding domain comprises: i) heavy chain variable domain complementarity determining region 1 (VH-CDR1) comprising the amino acid sequence of SEQ ID NO: 1 or an amino acid sequence having at least 80% homology to SEQ ID NO: 1; ii) VH-CDR2 comprising the amino acid sequence of SEQ ID NO: 2 or an amino acid sequence having at least 80% homology to SEQ ID NO: 2; and iii) VH-CDR3 comprising the amino acid sequence of SEQ ID NO: 3 or an amino acid sequence having at least 80% homology to SEQ ID NO: 3.

The BCMA-binding protein according to an embodiment of the present invention may exhibit specific binding activity to BCMA.

The chimeric antigen receptor (CAR) comprising the antigen-binding domain that specifically binds to BCMA according to an embodiment of the present invention may be expressed well in immune cells. As such, the immune cells expressing the BCMA-specific CAR may exhibit cytotoxicity specific to BCMA-expressing cells, and when introduced into a living body, may effectively treat a BCMA-expressing tumor.

The BCMA-binding protein according to an embodiment of the present invention may be used for diagnosis, prevention, prediction of prognosis, and treatment of diseases, including a number of cancers, autoimmune disorders and infectious diseases, in particular cancer diseases, in which BCMA is known to be involved.

It is to be understood that the effects of the present invention are not limited to the above-described effects, and include all effects that may be deduced from the configuration of the invention described in the detailed description or claims of the present invention.

BRIEF DESCRIPTION OF DRAWINGS

FIG. 2 is a schematic view showing the structures of an anti-BCMA CAR according to one embodiment of the present invention and a vector containing the same.

FIG. 3 shows the sequence and structure of an anti-BCMA CAR according to one embodiment of the present invention.

FIG. 4 shows the results of analyzing intracellular expression of an anti-BCMA CAR according to an embodiment of the present invention by using biotinylated BCMA.

FIG. 5 shows the results of analyzing intracellular expression of an anti-BCMA CAR according to an embodiment of the present invention by using biotinylated anti-human Fab antibody.

BEST MODE

Figure 1:
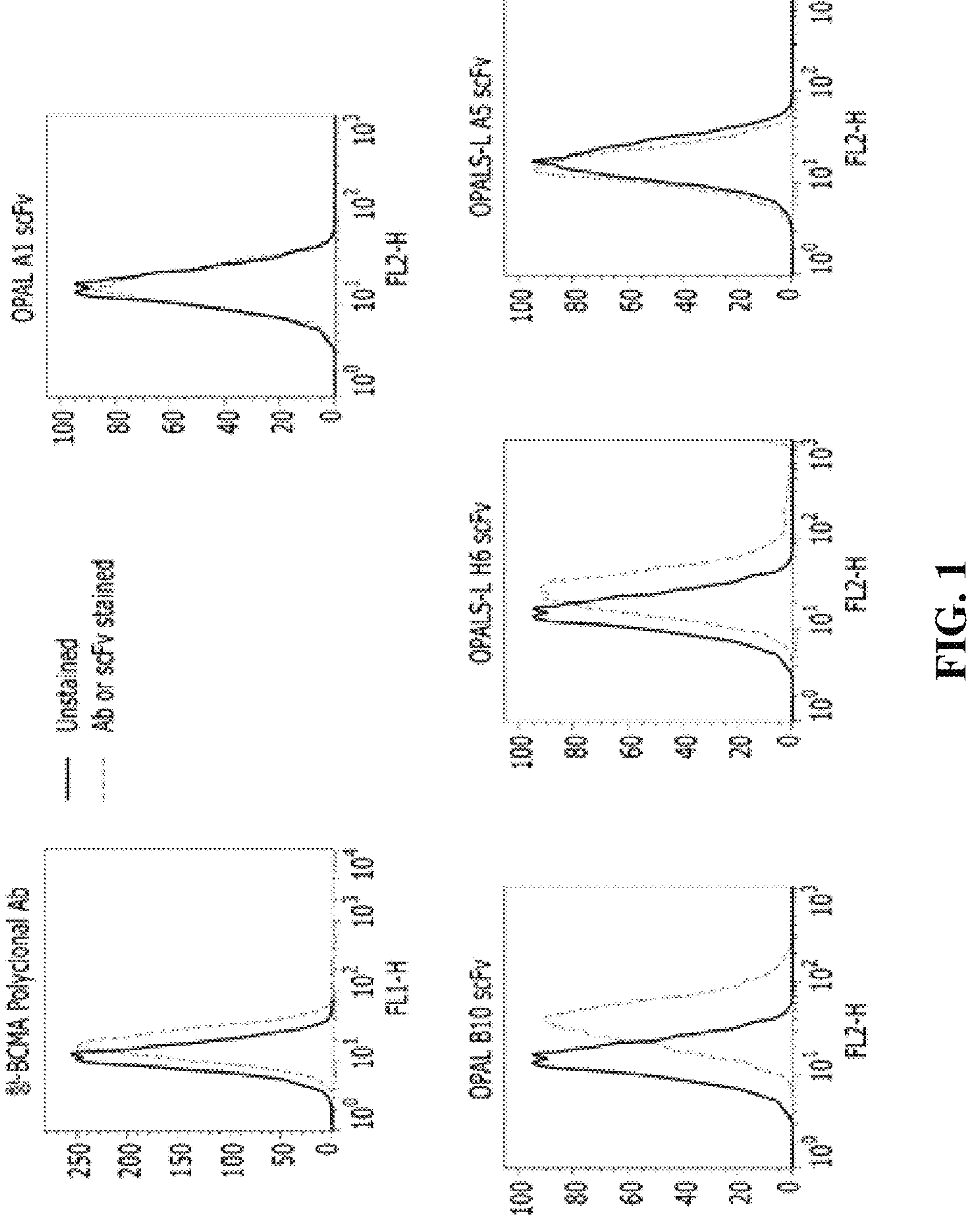
FIG. 1 shows the results of FACS performed to confirm BCMA-specific binding of anti-BCMA scFv antibody candidates.

Hereinafter, the present invention will be described with reference to the accompanying drawings. However, the present invention may be embodied in several different forms, and thus is not limited to the embodiments described herein. In addition, in the drawings, parts irrelevant to the description are omitted in order to clearly explain the present invention, and like reference numerals designate like parts throughout the specification.

Throughout the specification, it is to be understood that, when any part is referred to as being "connected (coupled, contacted or joined)" to another part, it includes not only a case where the part is "connected directly", but also a case where the part is "connected indirectly" with other members interposed therebetween. In addition, it is to be understood that, when any part is referred to as "comprising" a certain component, the part may further comprise other components, rather than excluding other components, unless otherwise stated.

The terms used herein are used only to describe specific embodiments, and are not intended to limit the present invention. Singular expressions include plural expressions unless the context clearly indicates otherwise. In the present specification, it should be understood that terms such as "comprise" and "have" are intended to denote the existence of mentioned characteristics, numbers, steps, operations, components, parts, or combinations thereof, but do not exclude the probability of existence or addition of one or more other characteristics, numbers, steps, operations, components, parts, or combinations thereof.

In the present specification, the term "domain" is used to indicate a unit having functional or structural characteristics. For example, a binding domain refers to any domain capable of recognizing or interacting with and specifically binding to a target molecule (e.g., an antigen). The BCMA-binding protein according to the present invention comprises a binding domain specific for the antigen BCMA. A domain according to the invention is preferably a polypeptide. Such a polypeptide may be a single polypeptide chain, or may be a module formed by combining parts of several polypeptide chains. These polypeptides may include proteinaceous parts and non-proteinaceous parts, wherein the non-proteinaceous parts may be chemical linkers or chemical cross-linking agents such as glutaraldehyde.

As used herein, "VH", "VL", "CDR", "Fv", "Fab", "Fab", "F(ab')2", "Fc", "VHH" and "VNAR" are generally fragments of native antibodies that are used interchangeably with the term "immunoglobulins". The basic four-chain antibody unit is a heterotetrameric glycoprotein composed of two identical light (L) chains and two identical heavy (H) chains. Each L chain is linked to an H chain by one covalent disulfide bond, while the two H chains are linked to each other by one or more disulfide bonds depending on the H chain isotype. Each H and L chain also has regularly spaced intra-chain disulfide bridges. Each H chain has, at the N-terminus, a variable domain (VH) followed by a constant domain at its end. In the case of mammalian immunoglobulin, α, δ and γ chains each have 3 CHs, and μ and ε isotypes each have 4 CHs. Each L chain has, at the N-terminus, a variable domain (VL) followed by a constant domain (CL) at its other end. The VL is aligned with the VH and the CL is aligned with the first constant domain of the heavy chain (CH1). Particular amino acid residues are known to form an interface between the light chain and heavy chain variable domains. The pairing of a VH and VL together forms a single antigen-binding site. Immunoglobulins can be classified according to the type of heavy chains included therein. For example, mammalian immunoglobulins including α, δ, ε, γ, and μ as heavy chains are divided into IgA, IGD, IgE, IgG, and IgM, respectively. Some linages of animals also have other types of immunoglobulins. For example, birds, amphibians, bony and cartilaginous fish show immunoglobulins with different types and/or numbers of heavy chain variable domains, and Camelidae and sharks show heavy chain-only immunoglobulins in which the numbers of constant domains are 2 and 5, respectively, and which comprise heavy chain variable domains, known as VHH and VNAR, respectively.

The term "variable" refers to the fact that certain segments of the variable domains differ extensively in sequence among antibodies. The variable domain mediates antigen binding and defines specificity of a particular antibody for its particular antigen. However, the variability is not evenly distributed throughout the variable domains, but is concentrated in three segments, known as hypervariable regions (HVRs) or complementarity-determining regions (CDRs), in both the light chain and heavy chain variable domains. In contrast, relatively highly conserved regions on the variable domains are called framework regions (FRs). The heavy and light chain variable domains of mammalian immunoglobulins include four FRs linked by three CDRs, respectively. The CDRs in each chain are closely located by the FR regions, thus forming the antigen-binding domain of the antibody together with the CDRs of the other chain. The constant domains are not directly involved in binding the antibody to an antigen, but become the recognition sites of the antibody when antibody-dependent cellular cytotoxicity is induced.

Fv is a minimal fragment of an antibody that contains a complete antigen recognition and binding site, and is composed of a dimer of VH and VL. Fab refers to a fragment including a light chain constant domain and CH1 in addition to Fv, and may be obtained by treating an IgG antibody with papain. Fab' includes a portion of the hinge (between CH1 and CH2) in addition to Fab, and F(ab')2, which may be obtained by treating an IgG antibody with pepsin, include a hinge portion linked by a disulfide bond, and thus includes a divalent binding site. The Fc region is a crystallizable constant region of an antibody not comprising an antigen-specific binding region, and is composed of two identical protein fragments. Fc regions of IgG, IgA and IgD antibody isotypes comprise the second and third constant domains (CH2-CH3) of the antibody heavy chain, and Fc regions of IgM and IgE antibody isotypes include the second, third and fourth constant domains (CH2-CH3-CH4) of the antibody heavy chain.

The amino acid sequences included herein may cover sequences having at least 80%, preferably at least 90%, more preferably at least 95%, most preferably at least 99% homology thereto, when a change is made such that a sequence difference appears while maintaining the binding properties of the binding protein according to the present invention. The change may be any one or more selected from addition, substitution, or deletion of at least one amino acid residue.

An isolated BCMA-binding protein according to one aspect of the present invention comprises an antigen-binding domain that binds specifically to BCMA, wherein the antigen-binding domain comprises: i) heavy chain variable domain complementarity determining region 1 (VH-CDR1) comprising the amino acid sequence of SEQ ID NO: 1 or an amino acid sequence having at least 80% homology to SEQ ID NO: 1; ii) VH-CDR2 comprising the amino acid sequence of SEQ ID NO: 2 or an amino acid sequence having at least 80% homology to SEQ ID NO: 2; and iii) VH-CDR3 comprising the amino acid sequence of SEQ ID NO: 3 or an amino acid sequence having at least 80% homology to SEQ ID NO: 3. Preferably, the BCMA-binding protein comprises: i) heavy chain variable domain complementarity determining region 1 (VH-CDR1) comprising the amino acid sequence of SEQ ID NO: 1; ii) VH-CDR2 comprising the amino acid sequence of SEQ ID NO: 2; and iii) VH-CDR3 comprising the amino acid sequence of SEQ ID NO: 3.

Here, the BCMA-binding domain may further comprise: i) light chain variable domain complementarity determining region 1 (VL-CDR1) comprising the amino acid sequence of SEQ ID NO: 4 or an amino acid sequence having at least 80% homology to SEQ ID NO: 4; ii) VL-CDR2 comprising the amino acid sequence of SEQ ID NO: 5 or an amino acid sequence having at least 80% homology to SEQ ID NO: 5; and iii) VL-CDR3 comprising the amino acid sequence of SEQ ID NO: 6 or an amino acid sequence having at least 80% homology to SEQ ID NO: 6. Preferably, the BCMA-binding domain may further comprise: i) light chain variable domain complementarity determining region 1 (VL-CDR1) comprising the amino acid sequence of SEQ ID NO: 4; ii) VL-CDR2 comprising the amino acid sequence of SEQ ID NO: 5; and iii) VL-CDR3 comprising the amino acid sequence of SEQ ID NO: 6.

BCMA (B-cell maturation antigen) is a member of the tumor necrosis factor receptor (TNFR) superfamily. BCMA binds to B-cell activating factor (BAFF) and a proliferation inducing ligand (APRIL). Among non-malignant cells, BCMA has been reported to be expressed mostly by plasma cells and subsets of mature B cells.

BCMA is expressed or overexpressed in a variety of human cancers. Examples of cancers that express or overexpress BCMA include Burkitt's lymphoma, diffuse large B-cell lymphoma (DLBCL), acute lymphocytic leukemia (ALL) lymphoma, Hodgkin's lymphoma, and multiple myeloma (MM). A polypeptide or protein comprising the BCMA-binding protein of the present invention can specifically recognize and bind to BCMA, thereby targeting BCMA-expressing cancer cells. This BCMA-binding protein is expected to be used in all procedures for diagnosis, prevention, prediction of prognosis, and treatment of diseases, including detection of cancer cells expressing BCMA, targeting and destruction of cancer cells expressing BCMA, reduction and elimination of cancer cells, promotion of penetration of immune cells or effector molecules or both into tumor sites, enhancement of anticancer responses, and prolongation of anticancer responses. The polypeptide or protein comprising the BCMA-binding protein may be combined with an additional polypeptide, protein or compound in order to increase the efficacy thereof when used for the above-described purposes. For example, the BCMA-binding protein may additionally comprise Fc (crystallizable fragment), conjugated drugs, molecular tags (e.g., fluorescent markers, protein tags, etc.) capable of facilitate tracking, and the like, alone or in combination.

The BCMA-binding protein may comprise a heavy chain variable domain (VH) comprising the amino acid sequence of SEQ ID NO: 7 or an amino acid sequence having at least 80% homology to SEQ ID NO: 7. Preferably, it may comprise a VH comprising the amino acid sequence of SEQ ID NO: 7. The BCMA-binding protein may further comprise may comprise a light chain variable domain (VL) comprising the amino acid sequence of SEQ ID NO: 8 or an amino acid sequence having at least 80% homology to SEQ ID NO: 8. Preferably, it may further comprise a VL comprising the amino acid sequence of SEQ ID NO: 8.

The BCMA-binding protein may comprise: a heavy chain variable domain (VH) comprising the amino acid sequence of SEQ ID NO: 7 or an amino acid sequence having at least 80% homology to SEQ ID NO: 7; and a light chain variable domain (VL) comprising the amino acid sequence of SEQ ID NO: 8 or an amino acid sequence having at least 80% homology to SEQ ID NO: 8. Preferably, it may comprise a VH comprising the amino acid sequence of SEQ ID NO: 7 and a VL comprising the amino acid sequence of SEQ ID NO: 8.

The BCMA-binding protein may further comprise a linker, and the linker, VH and VL may be arranged in any one order selected from among VH-linker-VL or VL-linker-VH, preferably VH-linker-VL, in the N-terminal to C-terminal direction. Here, the linker is a portion connecting different domains to each other, and may comprise 2 to 500 amino acids. The linker may consist of glycine and serine residues. Preferably, the linker may comprise $(Gly_xSer_y)_n$ (n sequences, each consisting of x glycine residues and y serine residues; x, y and n are each an integer ranging from 1 to 10). More preferably, the linker may comprise $(Gly_4\text{-}Ser_1)_n$, wherein n may be 1, 2, 3, 4, 5, or 6, preferably 3 or 4. Most preferably, the linker may comprise $(Gly_4\text{-}Ser_1)_3$ (i.e., GGGGSGGGGSGGGGS; SEQ ID NO: 17).

The BCMA-binding protein may comprise the amino acid sequence of SEQ ID NO: 9 or an amino acid sequence having at least 80% homology to SEQ ID NO: 9. Preferably, it may comprise the amino acid sequence of SEQ ID NO: 9.

The BCMA-binding protein may be any one selected from the group consisting of: i) an immunoglobulin selected from among IgA, IgD, IgE, IgG and IgM; ii) a native antibody fragment selected from among Fv, Fab, Fab', F(ab')2, VHH, and VNAR; iii) an engineered antibody selected from among scFv, dsFv, ds-scFv, (scFv)2, diabodies, triabodies, tetrabodies, and pentabodies; iv) ii) or iii) linked to Fc, at least one heavy chain constant domain, multimerization domain or chemical linker, or a combination thereof; and v) an anti-BCMA chimeric antigen receptor (CAR).

The BCMA-binding protein may have antigen specificity only for BCMA (i.e., monospecific), and may further have antigen specificity for one or more epitopes on BCMA other than epitopes to which the BCMA-binding site of the BCMA-binding protein binds, or antigen specificity for one or more antigens other than BCMA (i.e., multispecific). The BCMA-binding protein may comprise one antigen-binding site (monovalent), or may comprise one or more antigen-binding sites (multivalent). The BCMA-binding protein may be an engineered antibody comprising one or more sequences described herein. scFv is an antibody fragment consisting of VH and VL linked together by a linker peptide, dsFv is Fv stabilized by a disulfide bond, ds-scFv is scFv stabilized by a disulfide bond, (scFv)2 consists of two scFvs linked together. A diabody, a triabody, a tetrabody, and a pentabody are an scFv dimer, an scFv trimer, an scFv tetramer, and an scFv pentamer, respectively.

The BCMA-binding protein of the invention may be any type of immunoglobulin known in the art. For example, the BCMA-binding protein may be an antibody of any isotype, such as IgA, IgD, IgE, or IgG (e.g., IgG1, IgG2, IgG3, or IgG4), or IgM. The BCMA-binding protein may be monoclonal or polyclonal. The BCMA-binding protein may be a naturally occurring antibody isolated or purified from animals such as mice, rabbits, goats, horses, chicken, hamsters, and humans, or may be a synthetic antibody designed and genetically synthesized with reference to the sequence characteristics of the naturally occurring antibody. The BCMA-binding protein may be an engineered antibody, such as a humanized antibody or a chimeric antibody. The BCMA-binding protein may be in a monomeric or polymeric form. The BCMA-binding protein may include one or more chemical modifications, for example, addition of disulfide bonds, glycosylation, side chain-modified amino acids, methionine oxidation, asparagine or glutamine deamidation, γ-carboxylation, β-hydroxylation, sulfation, etc. The BCMA-binding protein may have any level of affinity or avidity for BCMA. The BCMA-binding protein may be any one selected from a mouse, rabbit, human, humanized or chimeric protein.

The anti-BCMA chimeric antigen receptor (CAR) molecule according to the present invention further comprises a transmembrane domain and an intracellular signaling domain, in addition to the above-described BCMA-binding domain.

In general, the CAR is a set of polypeptides, and when the CAR is expressed on immune cells, it allows these immune cells to specifically recognize and bind to their target molecule on cells (generally cancer cells) and enables this binding leads to activation of intracellular signaling in the immune cells. The CAR at least comprises an extracellular antigen-binding domain that recognizes a target antigen, a transmembrane domain, and an intracellular signaling domain. The intracellular signaling domain is preferably derived from a stimulatory molecule or a co-stimulatory molecule. The set of polypeptides may be in the form of a single-chain polypeptide, and or in the form of poly-chains which adhere to each other due to a switch that is dimerized or multimerized by stimulation. A stimulatory molecule refers to a molecule involved in signaling that activates an immune response in an antigen-specific manner, and a costimulatory molecule refers to a molecule that amplifies or reduces an initial signal of an immune cell in a non-antigen-specific manner. The intracellular signaling domain may comprise one or more signaling domains derived from a stimulatory molecule or a co-stimulatory molecule. It is possible for this signaling domain to induce the activation of, preferably, an immune cell that expresses the CAR. Here, the activation may induce initiating and/or increasing one or more of cell proliferation, differentiation into effector cells, cytokine secretion, cytotoxic substance secretion, phagocytosis, and induction of target cell death. The CAR may be a fusion protein comprising the extracellular antigen-binding domain, the transmembrane domain, and the intracellular signaling domain. The CAR may further comprise a signal peptide (or a leader sequence) at the N-terminus, and the signal peptide may be cleaved in the process in which the CAR is expressed and sits on the cell membrane.

The intracellular signaling domain may comprise a signaling domain derived from any one or more selected from among CD3ζ, FcγR, ICOS (CD278), 4-1BB (CD137), OX40 (CD134), CD27, CD28, IL-2Rβ, IL-15R-α, CD40, MyD88, DAP10, DAP12, MHC class I molecules, TNF receptor proteins, immunoglobulin-like proteins, cytokine receptors, integrins, SLAM protein, activating NK cell receptors, BTLA, Toll ligand receptors, CD2, CD7, CD30, CD40, CDS, ICAM-1, B7-H3, GITR, BAFFR, LIGHT, HVEM (LIGHTR), KIRDS2, SLAMF7, NKp80 (KLRF1), NKp44, NKp30, NKp46, CD19, CD4, CD8α, CD8β, IL2Rγ, IL7Rα, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and CD83-specific ligands. Preferably, the intracellular signaling domain may comprise any one or more selected from among CD3ζ and 4-1BB. Most preferably, the intracellular signaling domain may comprise both CD3ζ and 4-1BB.

The intracellular signaling domain may comprise any one or more selected from among: the amino acid sequence of SEQ ID NO: 10 or an amino acid sequence having at least 80% homology to SEQ ID NO: 10; and the amino acid sequence of SEQ ID NO: 11 or an amino acid sequence having at least 80% homology to SEQ ID NO: 11. Preferably, the intracellular signaling domain may comprise any one or more selected from among the amino acid sequence of SEQ ID NO: 10 and the amino acid sequence of SEQ ID NO: 11. More preferably, the intracellular signaling domain may comprise both the amino acid sequence of SEQ ID NO: 10 and the amino acid sequence of SEQ ID NO: 11.

The transmembrane domain may be derived from any one selected from among T-cell receptor (TCR) α chains, TCR β chains, CD3ζ, CD38, CD28, CD45, CD4, CD5, CD8, CD9, CD16, CD22, CD33, CD37, CD64, CD80, CD86, CD134, CD137, CD154, CD278, and CD314. Preferably, the transmembrane domain may be selected from among those capable of promoting dimerization of the anti-BCMA CAR molecule. For example, the transmembrane domain may be derived from CD3ζ, CD28 or CD8, more preferably CD8, most preferably CD8α. The transmembrane domain may comprise the amino acid sequence of SEQ ID NO: 12 or an amino acid sequence having 80% or more homology to SEQ ID NO: 12. Preferably, the transmembrane domain may comprise the amino acid sequence of SEQ ID NO: 12.

The anti-BCMA CAR molecule may further comprise a hinge domain, wherein the hinge domain may be located between the BCMA-binding protein and the transmembrane domain. The hinge domain may be derived from any one selected from among CD8, FcγRIIIα and IgG1, preferably from CD8, and more preferably from CD8α. The hinge domain may comprise the amino acid sequence of SEQ ID NO: 13 or an amino acid sequence having at least 80% homology to SEQ ID NO: 13.

The anti-BCMA CAR molecule may further comprise a signal peptide at the N-terminus. The signal peptide may be derived from any one selected from among CD8, IgG1 heavy chains, IgK light chains, and GM-CSF, preferably from CD8, and most preferably from CD8α. The signal peptide may comprise the amino acid sequence of SEQ ID NO: 14 or an amino acid sequence having at least 80% homology to SEQ ID NO: 14. Preferably, the signal peptide may comprise the amino acid sequence of SEQ ID NO: 14.

The anti-BCMA CAR may comprise the amino acid sequence of SEQ ID NO: 15 or an amino acid sequence having at least 80% homology to SEQ ID NO: 15. Preferably, the anti-BCMA CAR may comprise the amino acid sequence of SEQ ID NO: 15.

The anti-BCMA CAR may further comprise a linker connecting different peptide modules, domains, and the like. Here, the linker may comprise 2 to 500 amino acids as described above. The linker may be any one selected from among the above-mentioned linkers and the sequences shown in Table 1 below.

TABLE 1

| Linker sequence name | Amino acid sequence |
|---|---|
| Whitlow | GSTSGSGKPGSGEGSTKG (SEQ ID NO: 16) |
| Lk1 | GGGGSGGGGSGGGGS (SEQ ID NO: 17) |
| Lk2 | GGGGSGGGGSGGGGSGGGGS (SEQ ID NO: 18) |
| Lk3 | DGGGS(SEQ ID NO: 19) |
| Lk4 | TGEKP(SEQ ID NO: 20) |
| Lk5 | GGRR(SEQ ID NO: 21) |
| Lk6 | EGKSSGSGSESKVD(SEQ ID NO: 22) |
| Lk7 | KESGSVSSEQLAQFRS(SEQ ID NO: 23) |
| Lk8 | GGRRGGGS(SEQ ID NO: 24) |
| Lk9 | LRQRDGERP(SEQ ID NO: 25) |

TABLE 1-continued

| Linker sequence name | Amino acid sequence |
|---|---|
| Lk10 | LRQKDGGGSERP (SEQ ID NO: 26) |
| Lk11 | LRQKDGGGSGGGSERP(SEQ ID NO: 27) |
| Lk12 | GSTSGSGKPGSGEGSTKG(SEQ ID NO: 28) |

An isolated nucleic acid according to another aspect of the present invention may encode the above-described BCMA-binding protein. The nucleic acid may comprise an expression control sequence operably linked to a sequence encoding the BCMA-binding protein. The expression control sequence may comprise one or more of a promoter, an enhancer, a polyadenylation signal, an internal ribosome entry site (IRES), an intron, and other post-transcriptional regulatory factors. The expression control sequence may be selected to be suitable for regulating expression in a cell when the isolated nucleic acid encoding the BCMA-binding protein is introduced into the cell to express the BCMA-binding protein, as will be described later.

The nucleic acid may be introduced into a cell in the form of a vector. The vector may be selected from among DNA, RNA, plasmid, lentiviral, adenoviral, and retroviral vectors. Preferably, the vector may be selected from among a lentiviral vector and a retroviral vector, because the genes contained in the lentiviral vector and the retroviral vector may be inserted into the genomic DNA of the immune cell and stably expressed. Most preferably, the vector may be a lentiviral vector.

In the use of the nucleic acid in the form of a vector as described above, variations in the vector, that is, addition, modification and deletion of nucleotides, which may occur in a cloning process for introducing a specific sequence into the vector, or modification or introduction of components for increasing the convenience or performance of the vector, etc., are obvious to those skilled in the art, and thus detailed description thereof will be omitted.

A cell according to still another aspect of the present invention may comprise the nucleic acid encoding the BCMA-binding protein.

The cell according to still another aspect of the present invention may express the BCMA-binding protein.

Examples of the cell include eukaryotic and prokaryotic cells, including yeast, fungus, insect cells and mammalian cells. For example, the cells may be bacterial cells such as *E. coli*, or may be eukaryotic microbial cells such as *Saccharomyces cerevisiae, Schizosaccharomyces pombe, yarrowia, Pichia pastoris, Candida, Trichoderma reesei, Neurospora, Schwanniomyces, Kluyveromyces, Penicillium, Tolypocladium*, and *Aspergillus* hosts. The cell may be derived from a multicellular organism in order to be more suitable for expression of an antibody or the like in post-translational modification processes such as glycosylation, and a host cell suitable for the vector containing the nucleic acid encoding the BCMA-binding protein may be selected. For example, when a baculovirus vector is used, the cell may be derived from an organism appropriately selected from among *Spodoptera frugiperda, Aedes aegypti, Aedes albopictus, Drosophila melanogaster, Bombyx mori*, and the like. The BCMA-binding protein expressed in the cell may be isolated and purified for use. Preferably, this isolation and purification may be performed by isolating the BCMA-binding protein from the soluble fraction of the cell after intracellular expression, followed by purification using affinity chromatography, size exclusion chromatography, or the like, without being limited thereto. Since processes for expression (biosynthesis), separation and purification of antibodies, fusion proteins, etc. may be easily selected by those skilled in the art, and thus detailed description thereof will be omitted.

The cell may preferably be an immune cell. The immune cell may be any one selected from among T cell precursors, NK cell precursors, T cells, natural killer (NK) cells, natural killer T (NKT) cells, B cells, monocytes, macrophages, and dendritic cells. More preferably, the immune cell may be a T cell, most preferably a cytotoxic T lymphocyte.

When the cell is for administration to a patient, it may be any one of an autologous cell from the patient, an allogeneic cell, and a heterologous cell, wherein the heterologous cell may be a mammalian cell. In order to reduce the possibility of immune rejection, the cell is preferably allogeneic, most preferably autologous.

The cell may further comprise another agent that enhances the activity, suitability, efficiency and/or safety of the cell expressing the BCMA-binding protein. The agent may be a nucleic acid or a protein. The agent may be expressed as a molecule different from the BCMA-binding protein or a nucleic acid encoding the same, or may be contained in the same molecule. The agent may be, for example, one or more additional CARs, and the additional CARs may have the same target molecule, that is, may target different epitopes of BCMA, or target different target molecules. The different target molecules may be selected from among 5T4, alpha 5β1-integrin, 707-AP, AFP, ART-4, B7H4, BAGE, β-catenin/m, Bcr-abl, MN/CIX antigen, CA125, CAMEL, CAP-1, CASP-8, CD4, CD7, CD19, CD20, CD22, CD25, CD30, CD33, CD38, CD44 variant domain 6, CD123, CD135, CD138, CD269, CDC27/m, CDK4/m, CEA, CLEC12A, CT, Cyp-B, DAM, EGFR, ErbB3, ELF2M, EMMPRIN, EpCam, ETV6-AML1, G250, GAGE, GnT-V, Gp100, HAGE, HER-2/new, HLA-A*0201-R170I, HPV-E7, HSP70-2M, HST-2, hTERT (or hTRT), iCE, IGF-1R, IL-2R, IL-5, KIAA0205, LAGE, LDLR/FUT, MAGE, MART-1/melan-A, MART-2/Ski, MC1R, myosin/m, MUC1, MUM-1, MUM-2, MUM-3, NA88-A, natural killer group 2D, Lewis Y antigen, PAP, proteinase-3, p190 minor bcr-abl, Pml/RARα, PRAME, PSA, PSM, PSMA, RAGE, RU1 or RU2, SAGE, SART-1, SART-3, survivin, TEL/AML1, TGFβ, TPI/m, TRP-1, TRP-2, TRP-2/INT2, VEGF, WT1, NY-Eso-1, and NY-Eso-B, and may be molecules that are specifically expressed, in addition to BCMA in the BCMA-expressing cancer of the patient. The agent may be one or more agents that modulate or regulate immune cell function. The molecule that modulates or regulates immune cell function may be an inhibitory molecule, and the agent may be a substance that reduces the expression, function, or both, of the molecule. Examples of the inhibitory molecule include PD1, PD-L1, CTLA4, TIM3, CEACAM (e.g., CEACAM-1, CEACAM-3 and CEACAM-5, etc.), LAG3, VISTA, BTLA, TIGIT, LAIR1, CD160, 2B4, and TGFR-beta. The agent may be an inhibitory nucleic acid such as dsRNA, siRNA, or shRNA, an inhibitory protein or system such as a clustered regularly interspaced short palindromic repeat (CRISPR), transcription-activator-like effector nuclease (TALEN), or zinc finger endonuclease (ZFN), or a protein or small molecule comprising an antibody or binding site for the inhibitory molecule, and may inhibit the inhibitory molecule through binding. The agent may be one that regulates the survival of the cell. For example, if a side effect such as a cytokine storm occurs when the cell is administered to a patient, the agent may be a molecule capable of removing the administered cells or inducing apoptosis of the administered cell, in response to a specific substance, and examples thereof include those disclosed in U.S. Pat. Nos. 5,358,866, 9,393,292, and European Patent No. 2,836,511.

A composition having an anticancer effect according to yet another aspect of the present invention comprises either a cell comprising the nucleic acid encoding the above-described BCMA-binding protein, or a cell expressing the above-described BCMA-binding protein.

The composition may be used for the treatment of cancer with increased expression of BCMA. The composition may preferably be used for the treatment of multiple myeloma, Hodgkin's and non-Hodgkin's lymphoma, various leukemias, and glioblastoma.

It is apparent to those skilled in the art that the composition having an anticancer effect may contain, in addition to the immune cell, various additives such as pharmaceutically acceptable salts, carriers, excipients, vehicles, and other additives capable of further enhancing the therapeutic effect of the composition, and thus detailed description thereof will be omitted.

In the present invention, preferred pharmaceutical formulations can be determined in view of the present disclosure and general knowledge of formulation technology, depending on the intended route of administration, delivery format, and desired dosage. Regardless of the manner of administration, an effective dose can be calculated according to patient body weight, body surface area, or organ size. Further refinement of the calculations for determining the appropriate dosage for treatment involving each of the formulations described herein are routinely made in the art and is within the ambit of tasks routinely performed in the art. Appropriate dosages can be ascertained through use of appropriate dose-response data.

MODE FOR INVENTION

Hereinafter, examples of the present invention will be described in detail so that the present invention can be easily carried out by those of ordinary skill in the art to which the present invention pertains. However, the present invention may be embodied in various different forms and is not limited to the examples described herein.

Example 1. Construction of scFv Library and Selection of Anti-BCMA scFv Candidates

<Example 1-1> Construction of scFv Library

The scFv library was constructed according to the method disclosed in Korean Patent No. 10-0961392.

Briefly, a library was designed by using human VH3-23/VL1-g gene as a framework and inserting random sequences into complementarity determining regions (CDRs), and restriction enzyme cleavage sequences were introduced immediately after the leader sequence of the beta-lactamase gene in a plasmid vector having a beta-lactamase gene as a selection marker, thereby preparing a pFDV plasmid vector. The scFv gene library was inserted into the vector, and then *E. coli* was transfected with the vector and cultured, thereby constructing a library. Through this process, it was possible to improve the quality of the library by removing most of scFv gene sequences having an abnormal stop codon or frameshift from the library. After removal of errors from the cultured library, the sequences were amplified by polymerase chain reaction, and then the scFv gene library was recombined therefrom and inserted into the pComb3X phagemid vector. *E. coli* strain ER2537 was transfected with the phagemid vector, thus obtaining the final library. The library was cultured in 400 mL of SB (super broth) medium containing carbenicillin, and when the absorbance at 600 nm reached 0.5, 1013 CFU of VCSM13 helper phages were added thereto, followed by infection at 37° C. for 1 hour while stirring at 80 rpm. 70 μg/mL of kanamycin antibiotic was added thereto, followed by culturing overnight while stirring at 200 rpm at 30° C., thereby producing phages having scFv displayed on the surface thereof. The next day morning, the culture was centrifuged, and the phages in the culture were precipitated by adding 4% polyethylene glycol-8000 and 3% sodium chloride. The precipitated phages were dissolved in 50 ml of PBS buffer, and precipitated again in the same manner as described above, and finally dissolved in 2 ml of PBS buffer. The phage solution was centrifuged to remove foreign substances, thereby obtaining the phage scFv library. Generally, the final phage library contains $10^{13}$ CFU/ml or more of phage particles.

<Example 1-2> Anti-BCMA scFv Selection

10 μg/ml of BCMA was added to an immunotube and allowed to be adsorbed onto the surface of the tube for 1 hour, and then a 3% skim milk solution was added to the tube to protect a non-BCMA-adsorbed surface portion. After the tube was evacuated, $10^{12}$ CFU of antibody phage library dispersed in a 3% skim milk solution was added to the tube and allowed to bind to the antigen. Non-specifically bound phages were washed out three times with TBST (Tris buffered saline—Tween 20) solution, and then the remaining antigen-specific phage antibody was eluted using 100 mM triethylamine solution.

The eluted phages were neutralized with 1.0 M Tris-HCl buffer (pH 7.8), and then infected into *E. coli* ER2537 at 37° C. for 1 hour, and the infected *E. coli* cells were plated on carbenicillin-containing LB (Luria-Bertani) agar medium and cultured overnight at 37° C. The cultured *E. coli* cells were suspended in 3 ml of SB (super broth)-carbenicillin culture medium, and 15% glycerol was added thereto. A portion of the suspension was stored at −80° C., and 50 μl of the remainder was inoculated in 20 ml of SB-carbenicillin-2% glucose solution and cultured at 37° C. When the absorbance of the culture at 600 nm reached 0.5, only the bacterial cells were separated by centrifugation and suspended again in 20 ml of SB-carbenicillin medium, and 1012 PFU (plaque formation unit) of VCSM13 helper phages were added thereto, followed by culturing at 37° C. with slow stirring.

After 1 hour, 70 μg/ml kanamycin was added thereto, followed by culturing at 30° C. overnight with rapid stirring (at 250 rpm). On the next day, the culture was centrifuged, and then the above-described panning process was repeated using, as a library, 1 ml of the supernatant containing phage particles, thereby enriching antigen-specific clones.

Example 2. Expression and Purification of Anti-BCMA scFv Antibody

After about three or four rounds of repetitive panning, four antigen-specific candidate clones (OPAL A1, OPAL B10, OPALS-L A5 and OPALS-K H6) were obtained. *E. coli* cells containing each antibody gene were plated and incubated on carbenicillin-containing LB agar medium to obtain single colonies, which were then inoculated and incubated in 200 μl of SB-carbenicillin solution and treated with IPTG to induce expression of scFv protein in the periplasm of the *E. coli* cells. The *E. coli* cells were suspended in 40 μl of 1×TES (50 mM Tris, 1 mM EDTA, 20% Sucrose, pH 8.0), and then 60 μl of 0.2×TES solution was added thereto, followed by standing at 4° C. for 30 minutes or more. Then, the suspension was centrifuged to extract the periplasm into the supernatant.

<Example 2-1> Expression of Selected scFv Antibody Against BCMA

The four selected scFv-positive single-colony clones against BCMA were seed-cultured in 5 ml of carbenicillin-containing SB medium (30 g Bactotrytone, 20 g yeast extract, 10 g/L MOPS buffer) overnight, and then the culture was transferred to 500 ml of carbenicillin-containing SR medium. When the OD value at 600 nm reached about 0.5, IPTG was added thereto to a concentration of 1 mM, followed by culturing at 30° C. overnight, thereby expressing scFv antibody in the periplasm of *E. coli*. On the next day, the *E. coli* cells obtained through centrifugation were suspended in 1×TES buffer (50 mM Tris, 1 mM EDTA, 20% sucrose, pH 8.0), and then a 1.5-fold volume of 0.2×TES was added thereto, followed by mixing. The suspension was centrifuged to extract the periplasm.

<Example 2-2> Purification of Selected scFv Antibody 5 mM (final) $MgSO_4$ was added to the scFv antibody extracted from the periplasm, and the resultant material was mixed with Ni-NTA beads pre-equilibrated with PBS, followed by stirring for 1 hour under a cold storage to allow the antibody to bind to the Ni-beads. Thereafter, affinity chromatography was performed, and unbound protein was sufficiently washed with. After further sufficient washing with buffer containing 5 mM Imidazole, the bound scFv antibody was eluted using 200 mM imidazole buffer. The eluted antibody was dialyzed, and the purity thereof was checked by electrophoresis. The protein was quantified by BCA assay, and the amount of purified antibody was recorded, and then a constant amount of the antibody was dispensed and then frozen-stored.

<Example 2-3> FACS for Selection of Anti-BCMA scFv and Sequencing

Whether the scFv antibody extracted from the periplasm easily bind to BCMA on the cell surface was checked using a fluorescence-activated cell sorting (FACS) technique. Here, Raji cells, a B-cell lymphoma cell line well known to express BCMA, were used. Raji cells were cultured to $2\times10^6$ cells on the plate, and then separated from the plate by trypsin treatment and centrifuged. The cells thus prepared are washed PBS containing 3% BSA (w/v) at 4° C. for 1 hour, and then washed once with 1×PBS and centrifuged at 3000 rpm for 3 minutes, followed by incubation with each primary antibody (each experimental group: 6.2 μg/mL OPAL A1, 13.2 μg/mL OPAL B10, 21 μg/mL OPALS-L A5, and 20 μg/mL OPALS-K H6; positive control: 0.5 μg/mL anti-BCMA polyclonal antibody (biotinylated)). Next, the cells were washed three times with 1×PBS and then incubated with each secondary antibody (each experimental group: anti-HA-PE; positive control: Avidin-FITC) and washed twice with 1×PBS. The cells were diluted to a certain volume and then analyzed by fluorescence-activated cell sorting (FACSCalibur, BD Bioscience) (FIG. 1).

One finally selected BCMA antigen-specific antibody clone (OPAL B10, hereinafter referred to B10) was cultured overnight in 10 ml of carbenicillin-containing SB medium, and plasmid DNA was extracted therefrom using a plasmid miniprep kit and then the nucleotide sequence thereof was obtained through a capillary sequencing service (Macrogen Co.). The nucleotide sequence was translated into a protein sequence, and then CDR sequences were analyzed based on the Kabat protein sequence database and the international ImMunoGeneTics information system (IMGT) analysis method.

Cell lines and cultures used in Examples and Experimental Examples to be described later are as follows: 293T cells were cultured in DMEM (Thermofisher Scientific) containing 10% fetal bovine serum (FBS), 2 mM L-glutamine, 100 U/mL penicillin, and 100 μg/mL streptomycin. NCI-H929, RPMI 8226 and U266B1 cells were cultured in RPMI1640 medium containing 10% FBS, 2 mM L-glutamine, 100 U/mL penicillin, and 100 μg/mL streptomycin (Thermofisher Scientific). PBMCs were cultured in AIM-V medium containing 5% Immune Cell SR (Thermofisher Scientific).

Example 3. Preparation of pL-B10-BBz Plasmid

Gene fragment SEQ ID #1 and gene fragment SEQ ID #2 (Table 2), each containing the B10 nucleotide sequence, were synthesized by Integrated DNA Technologies. Overlap extension PCR was performed using the two gene fragments and primers SEQ ID #1 and #2 (Table 3) to obtain a PCR product. The PCR product treated with the restriction enzymes Xhol and EcoRV was inserted into the pLV-CD19-BBz plasmid (PNAS, 2016, Ma JSY) treated with the restriction enzymes Xhol and EcoRV, thus preparing pLV-B10-BBz (FIGS. 2 and 3).

TABLE 2

| Gene Fragment SEQ ID # | Sequence |
|---|---|
| #1 (SEQ ID NO: 29) | CTCGAGCTTTTGGAGTACGTCGTCTTTAGGTTGGGGGGAGG GGTTTTATGCGATGGAGTTTCCCCACACTGAGTGGGTGGAG ACTGAAGTTAGGCCAGCTTGGCACTTGATGTAATTCTCCTT GGAATTTGCCCTTTTTGAGTTTGGATCTTGGTTCATTCTCA AGCCTCAGACAGTGGTTCAAAGTTTTTTTCTTCCATTTCAG GTGTCGTGAGGAATTCGGTACCGCGGCCGCCCGGGGATCCA TGGCCTTACCAGTGACCGCCTTGCTCCTGCCGCTGGCCTTG CTGCTCCACGCCGCCAGGCCGGAGGTGCAGCTGTTGGAGTC TGGGGGAGGCTTGGTACAGCCTGGGGGGTCCCTGAGACTCT CCTGTGCAGCCTCTGGATTCACCTTTAGCGATTATTATATG AGCTGGGTCCGCCTGGCTCCAGGGAAGGGGCTGGAGTGGGT CTCAGCGATCTCTCATAGTAGTGGTAATACATATTACGCTG ATTCTGTAAAAGGTCGGTTCACCATCTCCAGAGACAATTCC AAGAACACGCTGTATCTGCAAATGAACAGCCTGAGAGCCGA GGACACGGCCGTGTATTACTGTGCGAAAAATAATTGGGGTT TCGACTACTGGGGCCAGGGTACACTGGTCACCGTGAGCTCA GGTGGAGGCGGTTCAGGCGGAGGTGGATCCGGCGGTGGCGG ATCGCAGTCTGTGCTGACTCAGCCACCCT |
| #2 (SEQ ID NO: 30) | CTGTGCTGACTCAGCCACCCTCAGCGTCTGGGACCCCCGGG CAGAGGGTCACCATCTCTTGTACTGGCTCTTCATCTAATAT TGGCAGTAATGATGTCACCTGGTACCAGCAGCTCCCAGGAA CGGCTCCCAAACTCCTCATCTATTCTGATAGTAAGCGGCCA AGCGGGGTCCCTGACCGATTCTCTGGCTCCAAGTCTGGCAC CTCAGCCTCCCTGGCCATCAGTGGGCTCCGGTCCGAGGATG AGGCTGATTATTACTGTGCTGCTTGGGATGCTAGCCTGAGT GGTTATGTCTTCGGCGGAGGCACCAAGCTGACGGTCCTAAC CACGACGCCAGCGCCGCGACCACCAACACCGGCGCCCACCA TCGCGTCGCAGCCCCTGTCCCTGCGCCCAGAGGCGTGCCGG CCAGCGGCGGGGGGCGCAGTGCACACGAGGGGGCTGGACTT CGCCTGTGATATCTACATCTGGGCGC |

TABLE 3

| Primer SEQ ID # | Sequence |
|---|---|
| #1 (SEQ ID NO: 31) | GATTAGTTCTCGAGCTTTTGGAGTACGT |
| #2 (SEQ ID NO: 32) | GGGCGCCCAGATGTAGATATCACAGGCGAAG |

Example 4. Preparation of Lentiviral Vector 293T cells were placed in a 150 mm culture dish (SPL) coated with poly-D-lysine and then cultured for 24 hours. The next day, after replacement with fresh 293T cell culture medium, transfection was performed with pMDL g/p (Gag/Pol expression), pRSV-Rev (Rev expression), pMDG.1 (envelope expression) and pLV-B10-BBz plasmids using Lipofectamine 2000 (Thermofisher Scientific). After 48 hours, the culture was collected, and the produced lentiviral vector was concentrated using Lenti-X Concentrator (Takara Inc.) and then suspended in 4% lactose solution. Next, the vector was filtered through a 0.2 μm syringe filter (Millipore) and then stored at −80° C.

Example 5. T-Cell Transformation and Expansion

Frozen human PBMCs were thawed and then washed twice with a washing solution containing CliniMACS PBS/EDTA buffer (Miltenyi Biotec) and 0.5% albumin (Green Cross). MACS CD4 microbeads and MACS CD8 microbeads (Miltenyi Biotec) were added and allowed to bind to the washed PBMCs for 30 minutes, and then T cells were separated through QuadroMACS™ separator (Miltenyi Biotec). The separated T cells were washed, and then suspended in medium and activated with T Cell TransAct™ (Miltenyi Biotec) and 100 IU/mL recombinant human IL-2 (BMI Korea). After 24 hours, the lentiviral vector was added to the activated T cells to reach MOI=3, followed by culturing overnight. The next day, the transduced T cells were washed and 100 IU/mL recombinant human IL-2 was added thereto. Then, the cells were added to a G-Rex 6M plate (Wilson Wolf) and mass culture of CAR-T cells was performed. The number of cells was determined based on a change in the concentration of glucose in the culture medium.

Experimental Example 1. Analysis of Anti-BCMA CAR Expression

CAR expression on the cell surface was analyzed by flow cytometry. $1\times10^6$ cells were washed twice with D-PBS, mixed with human BD Fc Block (BD Bioscience), and then incubated at room temperature for 10 minutes. In addition, PE-Cy7 mouse anti-human CD3 (BD Bioscience) antibody and biotinylated BCMA (Argo) or biotinylated anti-human Fab antibody were added to the cells, followed by incubation at room temperature for 15 minutes. The above sample was washed twice with D-PBS, and then fixable viability dye eFlour 780 (eBioscience) and Streptavidin-Alexa Fluor®647 (Biolegend) were added thereto, followed by incubation at room temperature for 15 minutes. After washing twice with D-PBS, the cells were resuspended in D-PBS, and CAR expression thereon was analyzed with a BD FACSVerse™ Flow Cytometer.

The results obtained using biotinylated BCMA are shown in FIG. 4, and the results obtained using biotinylated anti-human Fab antibody are shown in FIG. 5. It could be confirmed that the anti-BCMA CAR was expressed in the T cell (B10-BBZ CAR-T) group transformed with the vector containing the anti-BCMA CAR according to the Example of the present invention.

Figure 6:
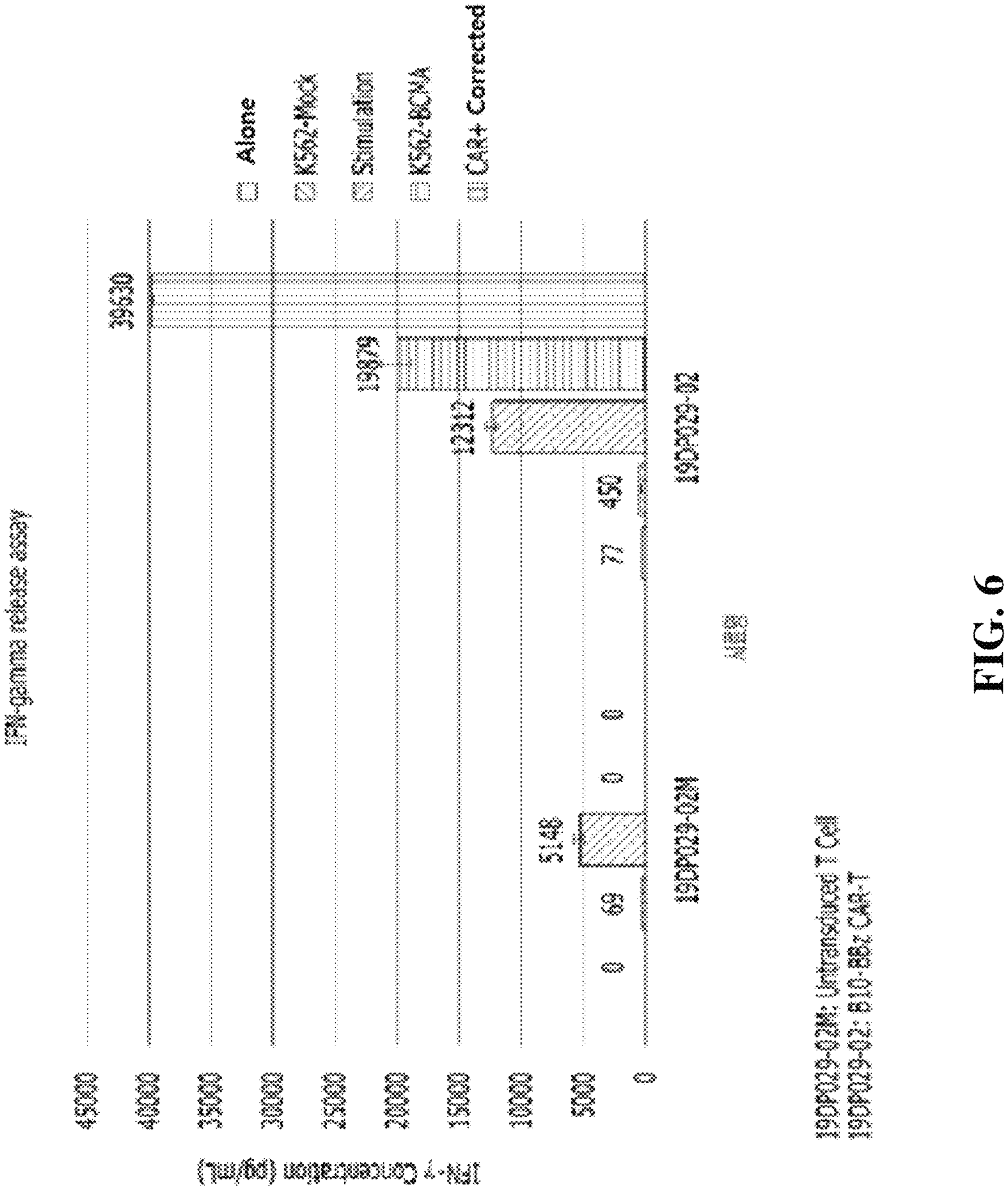
FIG. 6 shows the results of analyzing the IFN-γ secretion activity of anti-BCMA CAR T-cells according to one embodiment of the present invention.

Experimental Example 2. IFN-γ Release Assay $5.0\times10^4$ T cells were cultured alone or co-expressed with K562-Mock (K562 cells not expressing BCMA, 1:1 ratio) or K562-BCMA (K562 cells expressing BCMA, 1:1 ratio) in a cell incubator at 37° C. under 5% $CO_2$ for 24 hours. The amount of IFN-γ contained in the supernatant obtained by centrifugation of each sample at 500×g for 5 minutes was measured using DuoSet ELISA Ancillary Reagent Kit2 (R&D system) and human IFN-gamma DuoSet ELISA (R&D system), and the results are shown in FIG. 6. The data shown in FIG. 6 were classified into those obtained when only T cells were cultured (alone), those obtained when T cells were co-cultured with K562 cells not expressing BCMA (K562-Mock), those obtained when T cells were treated with stimulant (PMA/ionomycin) (Stimulation), those obtained when T cells were co-cultured with BCMA-expressing K562 cells (K562-BCMA), and those by correcting the amount of IFN-gamma measured in the K-562-BCMA group by the proportion of CAR-positive T cells (CAR+ corrected, % IFN-gamma/viable CAR-T cells).

As a result, it could be confirmed that, in the case of the cell groups into which the anti-BCMA CAR was introduced, the secretion of IFN-gamma, which is an indicator of cytotoxic activity, was higher in all the groups than in the control group into which that the anti-BCMA CAR was not introduced, and in particular, the secretion of IFN-gamma was significantly higher in a manner specific for BMCA, a molecule targeted by the CAR.

Figure 7:
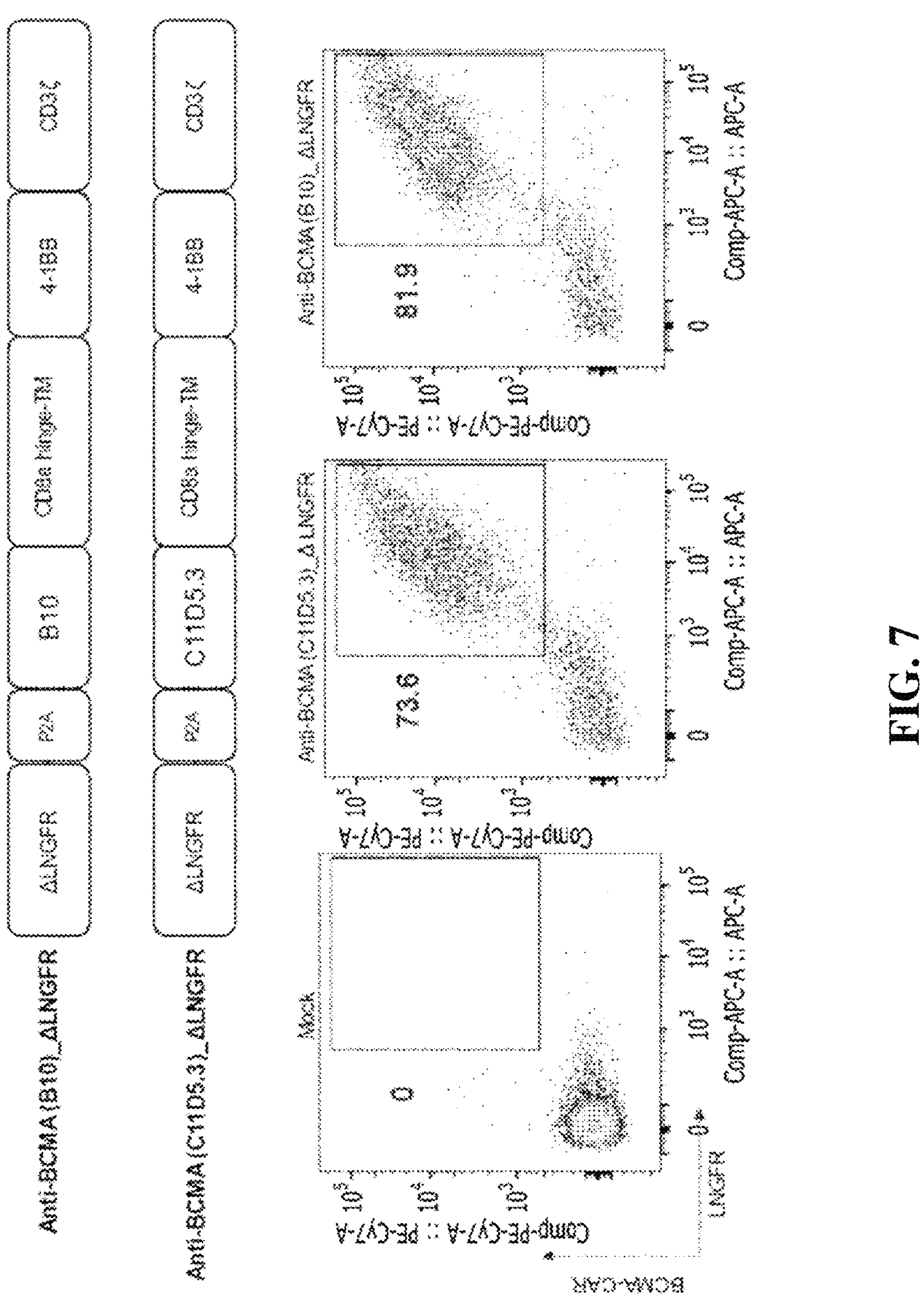
FIG. 7 shows the structures of anti-BCMA CARs produced using anti-BCMA (C11D5.3) and anti-BCMA (B10) scFvs, respectively, and depicts data showing expression of the anti-BCMA CARs on T-cells.

Example 3. Confirmation of T-Cell Transfection with CAR Composed of Each of Anti-BCMA (C11D5.3) and Anti-BCMA (B10) scFvs To evaluate the functional difference between already well-known anti-BCMA CAR (C11D5.3) and anti-BCMA (B10) CAR, the CARs as shown in FIG. 7 were constructed based on the C11D5.3 scFv sequence described in US Patent Publication No. US20150051266A1. 4 days after transduction of the CAR composed of each of anti-BCMA (C11D5.3) and anti-BCMA (B10) scFvs, transduced T cells were selected using LNGFR magnetic beads. 6 days after selection, the T cells were stained using APC-conjugated LNGFR Ab (Miltenyi biotec, clone: ME20.4-1.H4, Cat No. 130-113-418), biotinylated human BCMA/TNFRSF17 protein, FC, Avitag™, and streptavidin-PE-Cy7, and then the percentage of transduced cells was analyzed by flow cytometry. As a result, it could be confirmed that the purity of the transduced T cells was 70% or more, and that LNGFR and CAR were expressed at a ratio of almost 1:1 (FIG. 7).

Figure 8:
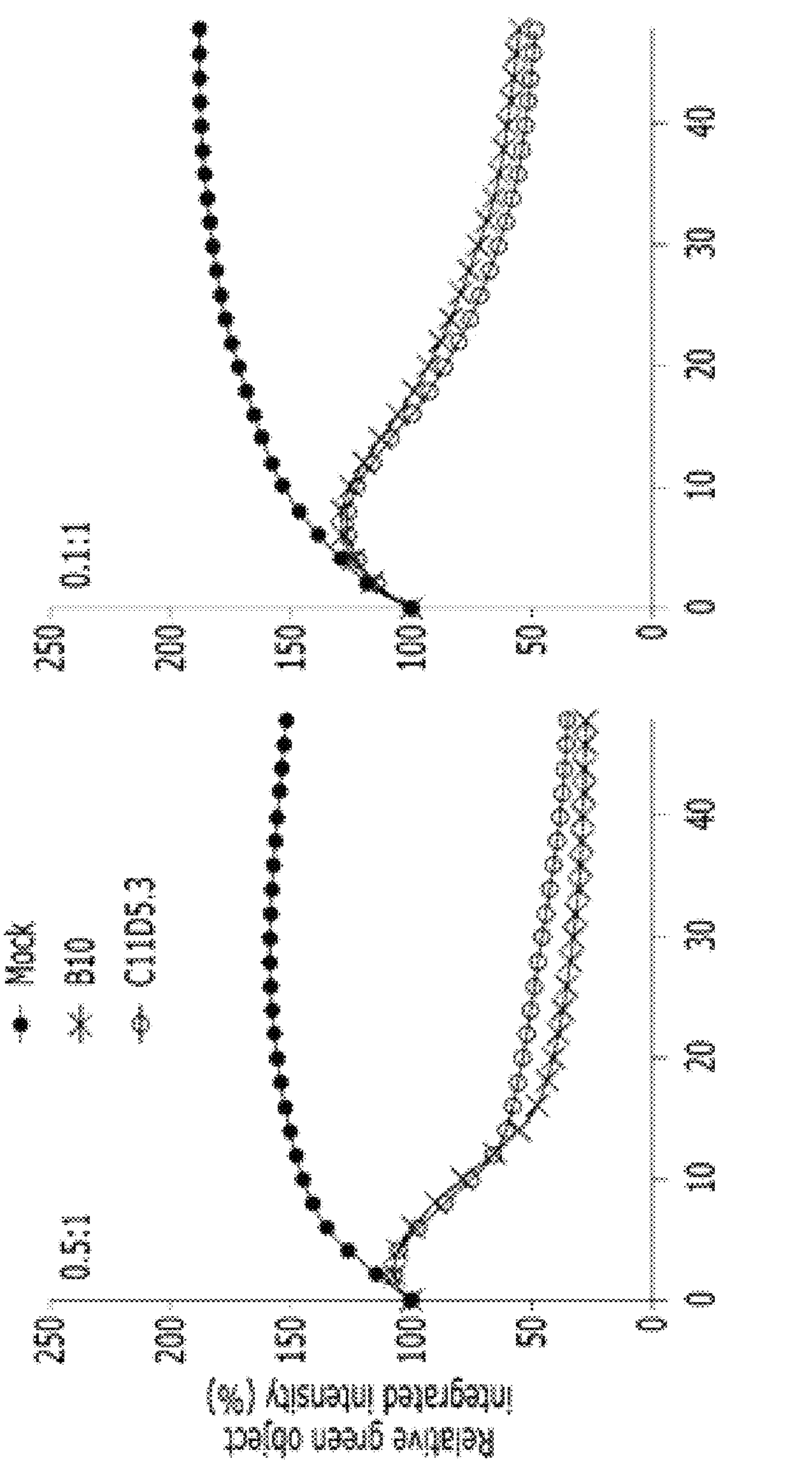
FIG. 8 depicts data showing the cytotoxicity of anti-BCMA CAR T-cells produced using anti-BCMA (C11D5.3) and anti-BCMA (B10) scFvs, respectively.
Figure 9:
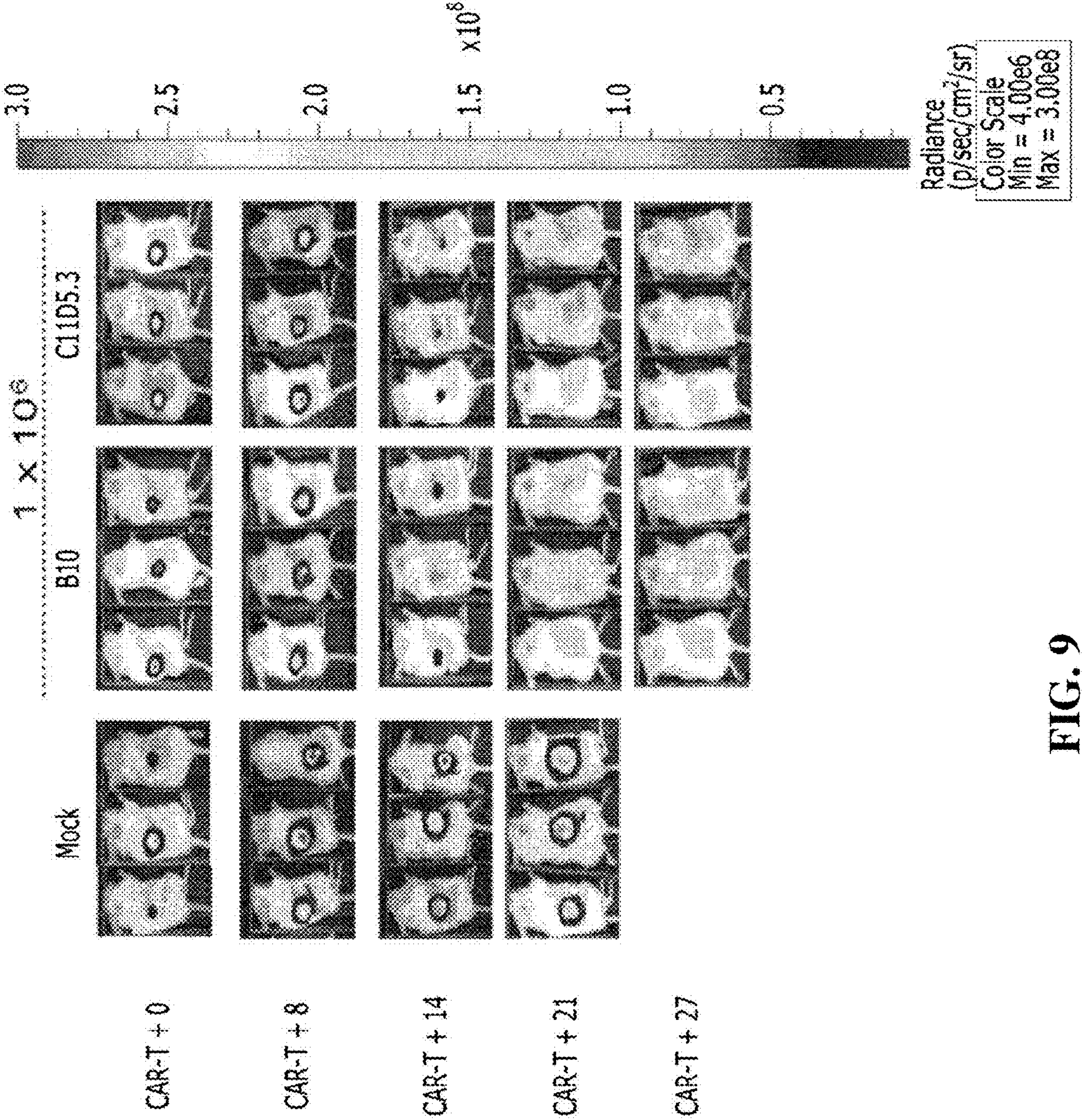
FIG. 9 depicts representative images (CAR T-cell dose: $1\times10^6$ cells) showing the in vivo anticancer efficacies of anti-BCMA CAR T-cells produced using anti-BCMA (C11D5.3) and anti-BCMA (B10) scFvs, respectively.
Figure 10:
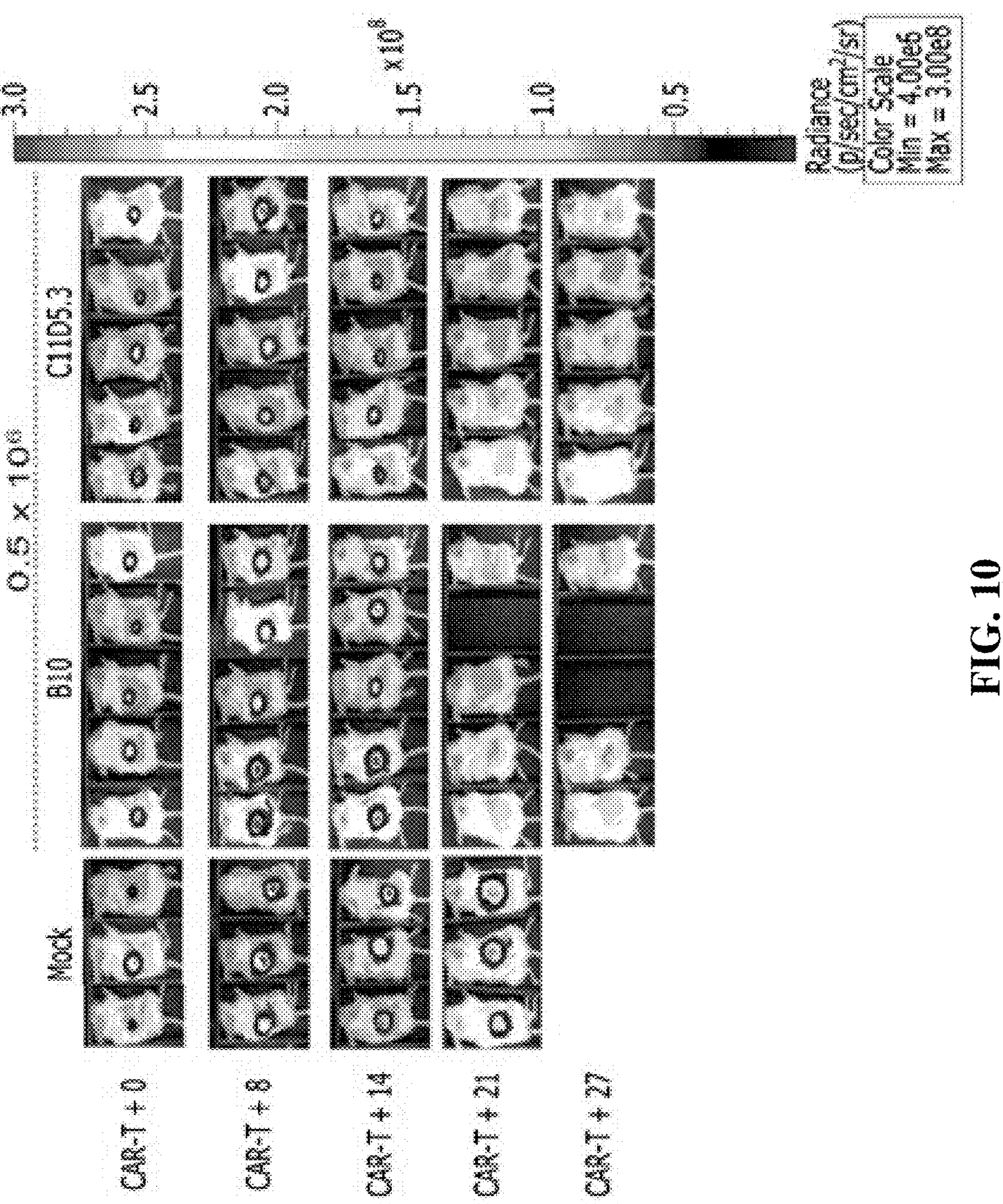
FIG. 10 depicts representative images (CAR T-cell dose: $0.5\times10^6$ cells) showing the in vivo anticancer efficacies of anti-BCMA CAR T-cells produced using anti-BCMA (C11D5.3) and anti-BCMA (B10) scFvs, respectively.
Figure 11:
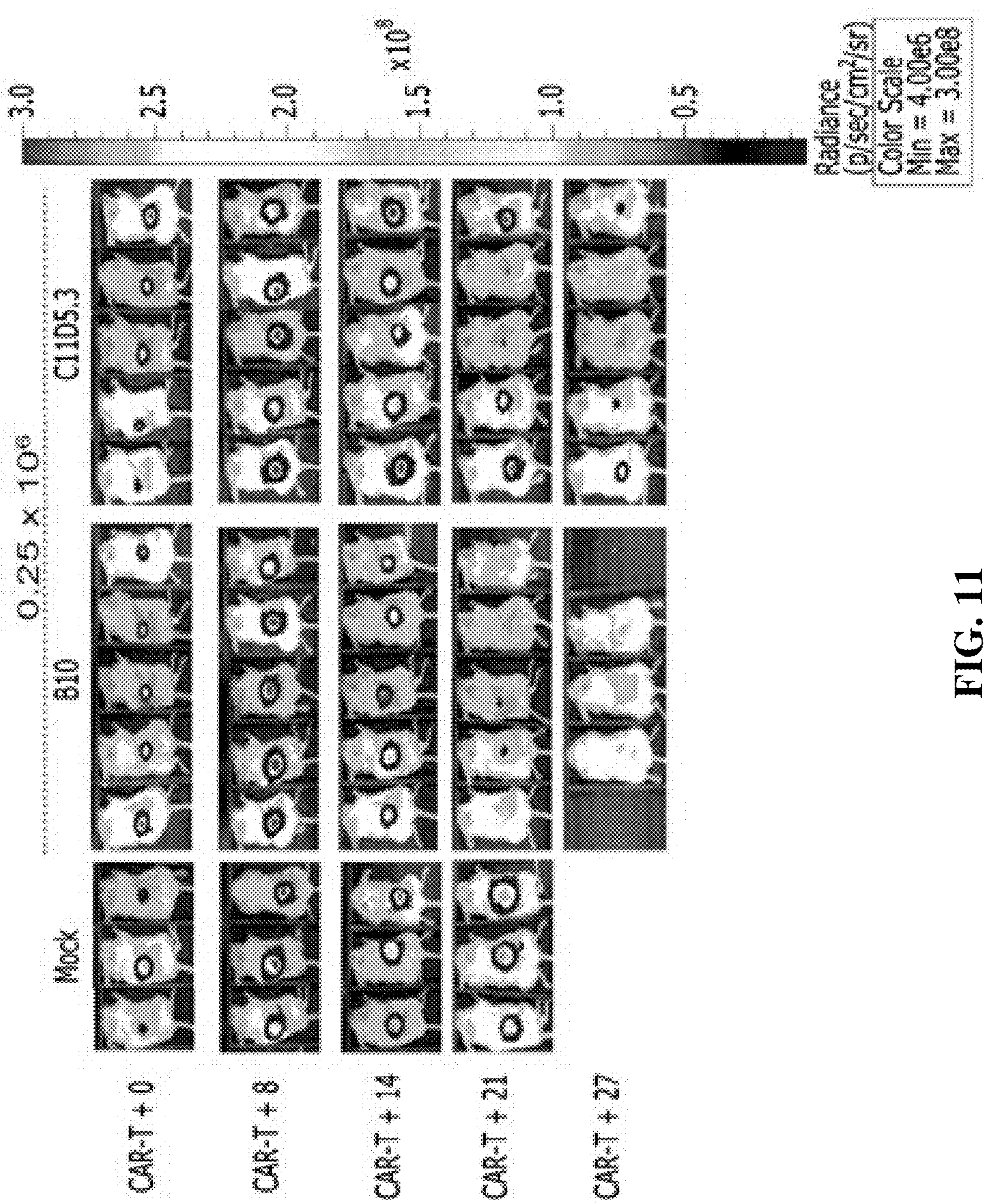
FIG. 11 depicts representative images (CAR T-cell dose: $0.25\times10^6$ cells) showing the in vivo anticancer efficacies of anti-BCMA CAR T-cells produced using anti-BCMA (C11D5.3) and anti-BCMA (B10) scFvs, respectively.
Figure 12:
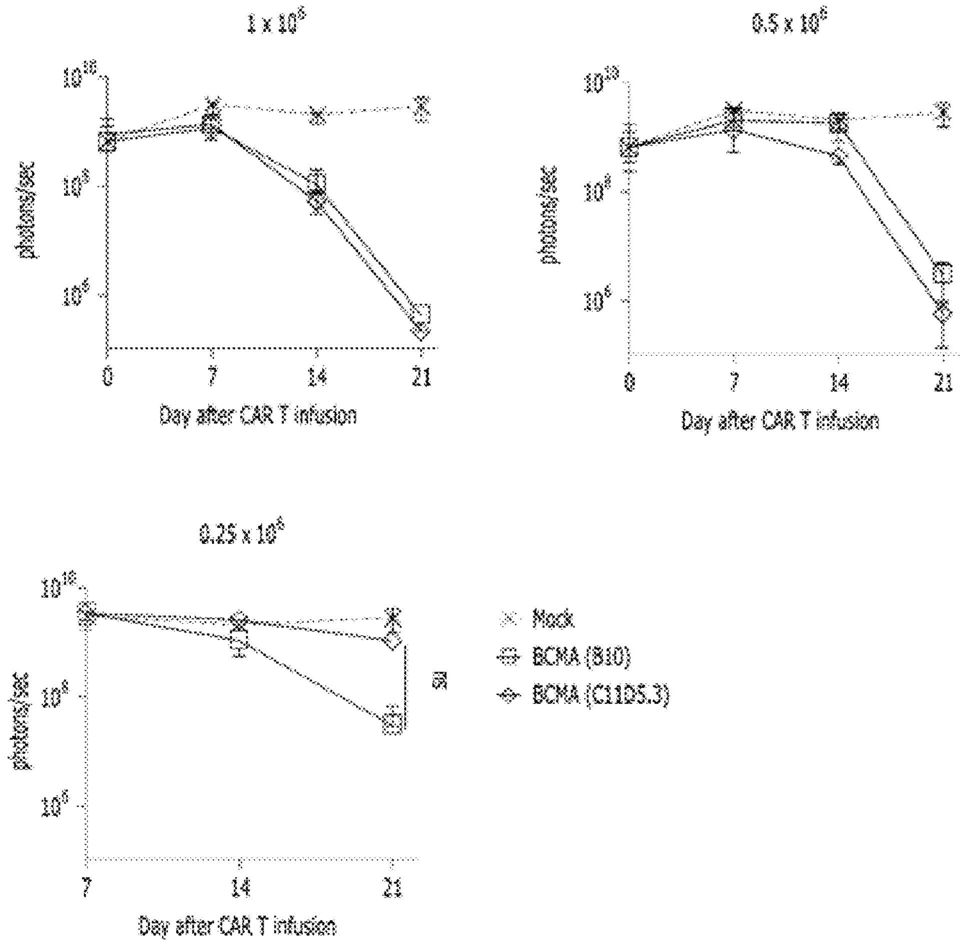
FIG. 12 depicts data showing the doses and in vivo anticancer efficacies of anti-BCMA CAR T-cells produced using anti-BCMA (C11D5.3) and anti-BCMA (B10) scFvs, respectively.

Experimental Example 4. Evaluation of Cytotoxicity of T Cells Transduced with CARs Composed of Each of Anti-BCMA (C11D5.3) and Anti-BCMA (B10) scFvs $1\times10^5$ multiple myeloma RPMI8226 cells (RPMI8226-GL) expressing BCMA and GFP were co-cultured with $0.5\times10^5$ or $0.1\times10^5$ Mock T cells, anti-BCMA (B10) CAR T cells, or anti-BCMA (C11D5.3) CAR T cells at 37° C. under 5% $CO_2$ for 48 hours. Cytotoxicity was evaluated by measuring the GFP fluorescence value at 2-hour intervals for 48 hours and normalizing the measured value to the value at 0 hours. As a result of the measurement, it was confirmed that anti-BCMA (B10) CAR T cells exhibited cytotoxicity similar to that of anti-BCMA (C11D5.3) CAR T cells (FIG. 8).

Experimental Example 5. Evaluation of In Vivo Anticancer Efficacies of Anti-BCMA (C11D5.3) CAR T-Cells and Anti-BCMA (B10) CAR T-Cells 12 days after injection of $1\times10^7$ RPMI8226-GL cells into S. Ceh, $1\times10^6$, $0.5\times10^6$, or $0.25\times10^6$ CAR T-cells were intravenously injected, and the anticancer efficacy of the T-cells was evaluated by measuring the luciferase activity expressed by the tumor cells at one-week intervals. As a result of the experiment, it was confirmed that the observed cytotoxicity was dependent on the amount of injected CAR T-cells, and that anticancer efficacy was similar between the anti-BCMA (C11D5.3) CAR T-cells and the anti-BCMA (B10) CAR T-cells (FIGS. 9 to 12).

Taken together, these results show that the T cells expressing the anti-BCMA CAR according to the present invention have high cytotoxic activity specific for BCMA, and exhibit high in vitro and in vivo anticancer efficacy comparable to that of the conventional BCMA CAR whose efficacy is well known.

The above description of the present invention is exemplary, and those of ordinary skill in the art will appreciate that the present invention can be easily modified into other specific forms without departing from the technical spirit or essential characteristics of the present invention. Therefore, it should be understood that the exemplary embodiments described above are exemplary in all aspects and are not restrictive. For example, each component described to be of a single type can be implemented in a distributed manner. Likewise, components described to be distributed can be implemented in a combined manner.

The scope of the present invention is defined by the following claims, and it shall be understood that all modifications and embodiments conceived from the meaning and scope of the claims and equivalents thereto are included in the scope of the present invention.

The invention claimed is:

1. An isolated BCMA (B-cell maturation antigen)-binding protein, comprising:

an antigen-binding domain that binds specifically to BCMA, wherein the antigen-binding domain comprises:

i) heavy chain variable domain complementarity determining region 1 (VH-CDR1) comprising the amino acid sequence of SEQ ID NO: 1;

ii) VH-CDR2 comprising the amino acid sequence of SEQ ID NO: 2;

iii) VH-CDR3 comprising the amino acid sequence of SEQ ID NO: 3;

iv) light chain variable domain complementarity determining region 1 (VL-CDR1) comprising the amino acid sequence of SEQ ID NO: 4;

v) VL-CDR2 comprising the amino acid sequence of SEQ ID NO: 5; and vi) VL-CDR3 comprising the amino acid sequence of SEQ ID NO: 6.

2. The isolated BCMA-binding protein of claim 1, wherein the isolated BCMA-binding protein comprises:

a heavy chain variable domain (VH) comprising the amino acid sequence of SEQ ID NO: 7; and a light chain variable domain (VL) comprising the amino acid sequence of SEQ ID NO: 8.

3. The isolated BCMA-binding protein of claim 2, wherein the isolated BCMA-binding protein further comprises a linker, and the linker, the VH and the VL are arranged in any one order selected from among VH-linker-VL and VL-linker-VH, in a N-terminal to C-terminal direction.

4. The isolated BCMA-binding protein of claim 1, wherein the isolated BCMA-binding protein comprises the amino acid sequence of SEQ ID NO: 9.

5. The isolated BCMA-binding protein of claim 1, wherein the isolated BCMA-binding protein is an scFv.

6. The isolated BCMA-binding protein of claim 5, wherein the isolated BCMA-binding protein is incorporated into an anti-BCMA chimeric antigen receptor, wherein the anti-BCMA chimeric antigen receptor further comprises an intracellular signaling domain, wherein the intracellular signaling domain comprises a signaling domain derived from any one or more selected from a group consisting of CD3ζ, FcγR, ICOS (CD278), 4-1BB (CD137), OX40 (CD134), CD27, CD28, IL-2Rβ, IL-15R-α, CD40, MyD88, DAP10, DAP12, MHC class I molecules, TNF receptor proteins, immunoglobulin-like proteins, cytokine receptors, integrins, SLAM protein, activating NK cell receptors, BTLA, and Toll ligand receptors.

7. The isolated BCMA-binding protein of claim 6, wherein the anti-BCMA chimeric antigen receptor further comprises a transmembrane domain, wherein the transmembrane domain is derived from any one selected from among T-cell receptor (TCR) α chains, TCR β chains, CD3ζ, CD3ε, CD28, CD45, CD4, CD5, CD8, CD9, CD16, CD22, CD33, CD37, CD64, CD80, CD86, CD134, CD137, CD154, CD278, and CD314.

8. The isolated BCMA-binding protein of claim 6, wherein the anti-BCMA chimeric antigen receptor further comprises a hinge domain, wherein the hinge domain is located between the BCMA-binding protein and the transmembrane domain and is derived from any one selected from among CD8, FcγIIIα, and IgG1.

9. The isolated BCMA-binding protein of claim 6, wherein the anti-BCMA chimeric antigen receptor further comprises a signal peptide at the N-terminus, wherein the signal peptide is derived from any one selected from among CD8, IgG1 heavy chains, IgK light chains, and GM-CSF.

10. The isolated BCMA-binding protein of claim 6, wherein the anti-BCMA chimeric antigen receptor comprises the amino acid sequence of SEQ ID NO: 15 or an amino acid sequence having at least 80% homology to SEQ ID NO: 15.

* * * * *